(12) United States Patent
Buechler

(10) Patent No.: US 7,524,635 B2
(45) Date of Patent: Apr. 28, 2009

(54) METHODS AND COMPOSITIONS FOR MEASURING NATRIURETIC PEPTIDES AND USES THEREOF

(75) Inventor: Kenneth F. Buechler, Rancho Santa Fe, CA (US)

(73) Assignee: Biosite Incorporated, San Diego, CA (US)

( * ) Notice: Subject to any disclaimer, the term of this patent is extended or adjusted under 35 U.S.C. 154(b) by 383 days.

(21) Appl. No.: 10/938,760

(22) Filed: Sep. 9, 2004

(65) Prior Publication Data

US 2005/0148024 A1 Jul. 7, 2005

Related U.S. Application Data

(63) Continuation-in-part of application No. 10/419,059, filed on Apr. 17, 2003, and a continuation-in-part of application No. PCT/US2004/026984, filed on Aug. 19, 2004, which is a continuation-in-part of application No. 10/645,874, filed on Aug. 20, 2003, which is a continuation-in-part of application No. 10/419,059, filed on Apr. 17, 2003.

(60) Provisional application No. 60/542,086, filed on Feb. 4, 2004.

(51) Int. Cl.
   *G01N 33/53* (2006.01)
(52) U.S. Cl. ........................................ 435/7.1
(58) Field of Classification Search ............... 435/4, 435/7.1, 6, 7.92, 973, 287.1; 436/514, 517
   See application file for complete search history.

(56) References Cited

U.S. PATENT DOCUMENTS

| | | |
|---|---|---|
| 4,900,662 A | 2/1990 | Shah et al. |
| 5,202,234 A | 4/1993 | Shah et al. |
| 5,206,140 A | 4/1993 | Marder et al. |
| 5,290,678 A | 3/1994 | Jackowski |
| 5,294,537 A | 3/1994 | Batt |
| 5,350,842 A | 9/1994 | Norgard |
| 5,352,587 A | 10/1994 | Chang et al. |
| 5,382,515 A | 1/1995 | Shah et al. |
| 5,382,522 A | 1/1995 | Shah et al. |
| 5,422,393 A | 6/1995 | Bricker et al. |
| 5,480,792 A | 1/1996 | Buechler et al. |
| 5,525,524 A | 6/1996 | Buechler et al. |
| 5,571,698 A | 11/1996 | Ladner et al. |
| 5,580,722 A | 12/1996 | Foulkes et al. |
| 5,604,105 A | 2/1997 | Jackowski |
| 5,631,171 A | 5/1997 | Sandstrom et al. |
| 5,679,526 A | 10/1997 | Buechler et al. |
| 5,683,885 A | 11/1997 | Kieback |
| 5,719,060 A | 2/1998 | Hutchens et al. |
| 5,747,274 A | 5/1998 | Jackowski |
| 5,768,163 A | 6/1998 | Smith, II |
| 5,786,163 A | 7/1998 | Hall |
| 5,795,725 A | 8/1998 | Buechler et al. |
| 5,824,799 A | 10/1998 | Buechler et al. |
| 5,843,690 A | 12/1998 | Gargan |
| 5,851,776 A | 12/1998 | Valkirs |
| 5,885,527 A | 3/1999 | Buechler |
| 5,894,063 A | 4/1999 | Hutchens et al. |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,020,208 A | 2/2000 | Hutchens et al. |
| 6,027,942 A | 2/2000 | Hutchens et al. |
| 6,028,055 A | 2/2000 | Lowe et al. |
| 6,057,098 A | 5/2000 | Buechler et al. |
| 6,107,623 A | 8/2000 | Bateman et al. |
| 6,113,855 A | 9/2000 | Buechler |
| 6,117,644 A * | 9/2000 | DeBold ................... 435/7.1 |
| 6,124,137 A | 9/2000 | Hutchens et al. |
| 6,124,430 A | 9/2000 | Mischak et al. |
| 6,143,576 A | 11/2000 | Buechler |

(Continued)

FOREIGN PATENT DOCUMENTS

EP 0542255 5/1993

(Continued)

OTHER PUBLICATIONS

Allwords.com, definition of "appreciable".*

(Continued)

*Primary Examiner*—Ann Y. Lam
(74) *Attorney, Agent, or Firm*—Wilson Sonsini Goodrich & Rosati PC

(57) ABSTRACT

The present invention describes compositions and methods designed to determine the presence or amount of natriuretic peptides, or their fragments, in a sample. The degradation of natriuretic peptides is an ongoing process that may be a function of, inter alia, the elapsed time between onset of an event triggering natriuretic peptide release into the tissues and the time the sample is obtained or analyzed; the quantity of proteolytic enzymes present; etc. This degradation can produce circulating amounts of natriuretic peptides having reduced or lost biological function. The present invention provides, inter alia, assays designed to accurately measure biologically active natriuretic peptides, and compositions to inhibit a previously unknown pathway for degradation of natriuretic peptides.

17 Claims, No Drawings

U.S. PATENT DOCUMENTS

| | | | |
|---|---|---|---|
| 6,156,521 | A | 12/2000 | Buechler et al. |
| 6,162,902 | A | 12/2000 | Mischak et al. |
| 6,171,870 | B1 | 1/2001 | Freitag |
| 6,174,686 | B1 | 1/2001 | Buechler et al. |
| 6,204,500 | B1 | 3/2001 | Whitehouse et al. |
| 6,225,047 | B1 | 5/2001 | Hutchens et al. |
| 6,235,489 | B1 | 5/2001 | Jackowski |
| 6,268,144 | B1 | 7/2001 | Koster |
| 6,309,888 | B1 | 10/2001 | Holvoet et al. |
| 6,461,828 | B1 | 10/2002 | Stanton et al. |
| 6,579,687 | B1 | 6/2003 | Buechler et al. |
| 6,586,244 | B2 | 7/2003 | Reinhard |
| 6,627,404 | B1 | 9/2003 | Buechler et al. |
| 6,627,457 | B2 | 9/2003 | Pandian et al. |
| 6,670,138 | B2 | 12/2003 | Gonzalez-Zulueta et al. |
| 6,756,483 | B1 | 6/2004 | Bergmann et al. |
| 6,828,107 | B2 | 12/2004 | Asada et al. |
| 6,839,343 | B2 | 1/2005 | Kelliher et al. |
| 6,939,678 | B1 | 9/2005 | Buechler et al. |
| 6,991,907 | B1 | 1/2006 | Buechler et al. |
| 7,341,838 | B2 | 3/2008 | Buechler et al. |
| 7,358,055 | B2 | 4/2008 | Valkirs et al. |
| 7,361,473 | B2 | 4/2008 | Valkirs et al. |
| 2003/0022235 | A1 | 1/2003 | Dahlen et al. |
| 2003/0119064 | A1 | 6/2003 | Valkirs et al. |
| 2003/0199000 | A1 | 10/2003 | Valkirs et al. |
| 2003/0211544 | A1 | 11/2003 | Buechler et al. |
| 2003/0219734 | A1 | 11/2003 | Buechler |
| 2004/0121343 | A1 | 6/2004 | Buechler et al. |
| 2004/0121350 | A1 | 6/2004 | Anderberg et al. |
| 2004/0126767 | A1 | 7/2004 | Anderberg et al. |
| 2004/0167341 | A1 | 8/2004 | Haffner et al. |
| 2004/0171064 | A1 | 9/2004 | Dahlen et al. |
| 2004/0176914 | A1 | 9/2004 | Buechler et al. |
| 2004/0203083 | A1 | 10/2004 | Buechler et al. |
| 2004/0209307 | A1 | 10/2004 | Valkirs et al. |
| 2004/0219509 | A1 | 11/2004 | Valkirs et al. |
| 2004/0253637 | A1 | 12/2004 | Buechler et al. |
| 2005/0164317 | A1 | 7/2005 | Buechler et al. |
| 2005/0181386 | A1 | 8/2005 | Diamond et al. |
| 2005/0244902 | A1* | 11/2005 | Gotze et al. ............... 435/7.92 |
| 2005/0255484 | A1 | 11/2005 | Valkirs et al. |
| 2006/0051825 | A1 | 3/2006 | Buechler et al. |
| 2006/0105419 | A1 | 5/2006 | Blankenberg et al. |
| 2007/0196880 | A1 | 8/2007 | Buechler et al. |
| 2007/0218498 | A1 | 9/2007 | Buechler et al. |
| 2007/0224643 | A1 | 9/2007 | McPherson et al. |
| 2007/0269836 | A1 | 11/2007 | McPherson |
| 2008/0045444 | A1 | 2/2008 | Whittaker |
| 2008/0118924 | A1 | 5/2008 | Buechler |

FOREIGN PATENT DOCUMENTS

| | | |
|---|---|---|
| EP | 1016867 | 7/2000 |
| WO | WO 91/09627 | 7/1991 |
| WO | WO 92/05173 A1 | 4/1992 |
| WO | WO 00/18801 | 4/2000 |
| WO | WO 2000/022439 A2 | 4/2000 |
| WO | WO 00/35951 A1 | 6/2000 |
| WO | WO 2000/018801 A3 | 7/2000 |
| WO | WO 00/52476 | 9/2000 |
| WO | WO 2000/022439 A3 | 11/2000 |
| WO | WO 01/14885 | 3/2001 |
| WO | WO 2001/014885 A3 | 2/2002 |
| WO | WO 02/083913 | 10/2002 |
| WO | WO 02/089657 | 11/2002 |
| WO | WO 03/002553 | 1/2003 |
| WO | WO 03/016910 | 2/2003 |
| WO | WO 2002/089657 A3 | 2/2003 |
| WO | WO 2003/002553 A3 | 3/2003 |
| WO | WO 03/035065 A1 | 5/2003 |
| WO | WO 03/035644 A1 | 5/2003 |
| WO | WO 2005/007653 A2 | 1/2005 |
| WO | WO 2005/007653 A3 | 3/2005 |

OTHER PUBLICATIONS

Huttunen et al., Coregulation of neurite outgrowth and cell survival by amphoterin and S100 proteins through receptor for advanced glycation end products (RAGE) activation. The Journal of Biological Chemistry, 275:40096-40105, 2000.

Mussack et al., Early cellular brain damage and systemic inflammatory response after cardiopulmonary resuscitation or isolated severe head trauma: a comparative pilot study on common pathomechanisma. Resuscitation, 49:193-199, 2001.

Yakoviev et al., Activation of CPP32-Like caspases contributes to neuronal apoptosis and neurological dysfunction after traumatic brain injury. The Journal of Neuroscience, 17(19): 7415-724, 1997.

International Search Report for international application No. PCT/US04/26984.

Notice of References Cited, PTO-892, Part of Paper No. 20041202 from U.S. Appl. No. 10/225,082 filed Aug. 20, 2002.

Harter et al., Caspase-3 activity is present in cerebrospinal fluid from patients with traumatic brain injury. Journal of Neuroimmunology, 121:76-78, 2001.

Cassin et al., È realizzabile una strategia operative piu efficace per la gestione in urgenza del paziente con dolore toracico acuto?, Ital Heart J Suppl, Feb. 2000, pp. 186-201, vol. 1.

Futterman et al., *Novel Markers in the Acute Coronary Syndrome*: BNP, IL-6, PAPP-A, American Journal of Critical Care, Mar. 2002, pp. 168-172, vol. 11, No. 2.

Hunt et al., *Immunoreactive amino-terminal pro-brain natriuretic peptide (NT-PROBNP): a new marker of cardiac impairment*, Clinical Endocrinology, 1997, pp. 287-296, vol. 47.

Sagnella et al., *Measurement and significance of circulating natriuretic peptides in cardiovascular disease*, Clinical Science, Nov. 1998, pp. 519-529, vol. 95, No. 5.

Sonel et al., Prospective Study Correlating Fibrinopeptide A, Troponin I, Myoglobin, and Myosin Light Chain Levels with Early and Late Ischemic Events in Consecutive Patients Presenting to the Emergency Department with Chest Pain, Circulation, Sep. 5, 2000, pp. 1107-1113, vol. 102, No. 10.

Greenberg, Angiogenesis and stroke, Drug News and Perspectives, 11(5):265-270, 1998. (Abstract only.).

Meester et al., In vivo inhibition of dipeptidyl peptidase IV activity by pro-pro-diphenyl-phosphonate (prodipine), Biochemical Pharmacology, 54:173-179, 1997.

Mills et al., Sustained hemodynamic effects of an infusion of nesiritide (human b-type natriuretic peptide) in heart failure, Journal of the American college of cardiology, 34(1):155-162, 1999.

Yakovlev et al., Activation of CPP32-like caspases contributes to neuronal apoptosis and neurological dysfunction after traumatic brain injury, The journal of neuroscience, 17(19):7415-7424, 1997.

Allwords.com., Definition of "Appreciable".

Bidzseranova et al., Structure-activity studies on the effects of atrial natriuretic peptide, brain natriuretic peptide and their analogs on fear-motivated learning behavior in rats. Neuropeptides, 23:61-65, 1992.

Hunter et al., "Analysis of Peptides Derived from Pro Atrial Natriuretic Peptide That Circulate in Man an Increase in Heart Disease", Scand J. Clin Lab Invest 56, 205-216 (1998).

Norman et al., Degradation of brain natriuretic peptide by neutral endopeptidase: Species specific sites of proteolysis determined by mass spectrometry. Biomedical and Biophysical Research Communications, 175(1): 22-30, 1991.

Vesley et al., "Negative Feedback of Atrial Natriuretic Peptides", Journal of Clinical Endocrinology and Metabolism, vol. 78, No. 5, 1128-1134 (1994).

Fonarow et al., "Combining Natriuretic Peptides and Necrosis Markers in Determining Prognosis in Heart Failure," Reviews in Cardiovascular Medicine, 2003, Suppl. 4, vol. 4.

Richards et al., "Neuroendocrine prediction of left ventricular function and heart failure after acute myocardial infarction," Heart, 1999, pp. 114-120, vol. 81.

Saady et al., "Left appendage: structure function, and role in thromboembolism," Heart, 1999, pp. 547-555, vol. 82.
Cala, Computerized axial tomography in the detection of brain damage. Medical Journal of Australia, 2(11): 616-620, 1980.
Cuzzocrea et al., Effects of tempol, a membrane-permeable radical scavenger, in a gerbil model of brain injury. Brain Research, 875:96-106, 2000.
Griffin et al., The inhibition of myeloperoxidase by ceruloplasmin can be reversed by anti-myeloperoxidase antibodies. Kidney International, 55:917-925, 1999.
Minota et al., Circulating myeloperoxidase and anti-myeloperoxidase antibody in patients with vasculitis. Scand J Rheumatol, 28:94-99, 1999.
Montaner et al, Matrix metalloproteinase expression after human cardioembotic strike. Stroke, 32:1759-1766, 2001.
Stronglin, *Laboratory diagnosis of viral infections, sensitivity, specificity, and predictive value of diagnostic tests: Definitions and clinical applications*. Lennette et al. eds., New York: Marcel Dekker, Inc., p. 211-219, 1992.
Tervaert, The value of serial ANCA testing during follow-up studies in patients with ANCA-associated vasculitides: A review. Journal of Nephrology, 9(5): 232-240, 1996.
International Search Report and the Written Opinion of the International Searching Authority from PCT Application No. PCT/US04/12024.
Bonow, R.O., "New insights into the cardiac natriuretic peptides." *Circulation* 93:1946-1950, (1996).
Cagney and Emili, "De novo peptide sequencing and quantitative profiling of complex protein mixtures using mass-coded abundance tagging." *Nature Biotechnol.* 20: 163-170, (2002).
Cannon et al., "Invasive versus conservative strategies in unstable angina and non-Q-wave myocardial infarction following treatment with Tirofiban: Rationale and study design of the international TACTICS-TIMI 18 trial." *Am. J. Cardiol.* 82: 731-6, (1998).
Cheng et al., "A Rapid bedside test for B-type peptide predicts treatment outcomes in patients admitted for decompensated heart failure: A pilot study." *J. Am. Coll. Cardiol.* 37: 386-91, (2001).
Cho et al., "Natriuretic peptides and their therapeutic potential." *Heart Dis.* 1: 305-28, (1999).
Cwirla et al., "Peptides on phage: A vast library of peptides for identifying ligands." *Proc. Natl. Acad. Sci. USA* 87, 6378-82, (1990).
Davidson et al., "C-Type natriuretic peptide." *Circulation* 93:1155-9, (1996).
Devlin et al., "Random peptide libraries: A source of specific protein binding molecules." *Science* 249, 404-6, (1990).
Fischer et al., "Evaluation of a new, rapid bedside test for quantitative determination of B-Type natriuretic peptide." *Clin. Chem.* 47: 591-594, (2001).
Gobinet-Georges et al. "Stability of brain natriuretic peptide (BNP) in human whole blood and plasma." *Clin. Chem. Lab. Med.* 38: 519-23, (2000).
Hamm et al., "Benefit of abciximab in patients with refractory unstable angina in relation to serum troponin T levels." *N. Engl. J. Med.* 340: 1623-9, (1999).
Hartree, "Determination of protein: A modification of the lowry method that gives a linear photometric response." *Anal Biochem* 48: 422-427, (1972).
Hunt et al., "The role of the circulation in processing pro-Brain natriuretic peptide (proBNP) to amino-terminal BNP and BNP-32." *Biochem. Biophys. Res. Comm.* 214: 1175-83, (1995).
Hunt et al., "The amino-terminal portion of pro-Brain natriuretic peptide (Pro-BNP) circulates in human plasma." *Peptides* 18: 1475-81, (1997).
Huse et al., "Application of a Filamentous phage pVII fusion protein system suitable for efficient production, screening, and mutagenesis of F(ab) antibody fragments." Journal of Immunology, 140: 3914-3920, (1992).
Issaq et al., "SELDI-TOF MS for diagnostic proteomics." *Anal. Chem.* 75: 149A-155A, (2003).
Issaq et al., "The SELDI-TOF MS approach to proteomics: Protein profiling and biomarker identification." *Biochem. Biophys. Res. Commun.* 292: 587-92, (2002).
Kalra et al., "Myocardial production of C-Type natriuretic peptide in chronic heart failure." *Circulation* 107: 571-3, (2003).
Lowry et al., "Protein measurement with the folin phenol reagent." *J. Biol. Chem.* 193: 265, (1951).
Merchant and Weinberger, "Recent advancements in surface-enhanced laser desorption/ionization-time of flight-mass spectrometry." *Electrophoresis* 21: 1164-67, (2000).
Morrow et al., "Cardiac troponin I for stratification of early outcomes and the efficacy of enoxaparin in unstable angina: A TIMI-11B substudy." *J. Am. Coll. Cardiol.* 36: 1812-7, (2000).
Motwani et al., "Plasma brain natriuretic peptide as an indicator for angiotensin-converting-enzyme inhibition after myocardial infarction." *Lancet* 341: 1109-13, (1993).
Murdoch et al. "Brain natriuretic peptide is stable in whole blood and can be measured using a simple rapid assay: Implications for clinical practice." *Heart* 78: 594-7, (1997).
Ng and Ilag, "Biomedical applications of protein chips." *J. Cell Mol. Med.* 6: 329-340, (2002).
Norman et al. "Degradation of brain natriuretic peptide by neutral endopeptidase: Species specific sites of proteolysis determined by mass spectrometry." *Biochem. Biophys. Res. Commun.* 28: 175: 22-30, (1991).
Prickett et al., "Identification of amino-terminal Pro-C-Type natriuretic peptide in human plasma." *Biochem. Biophys. Res. Commun.* 286:513-7, (2001).
Ridker et al., "Inflammation, pravastatin, and the risk of coronary events after myocardial infarction in patients with average cholesterol levels." *Circulation* 98: 839-44 (1998).
Scott and Smith, "Searching for peptide ligands with an epitope library." *Science* 249, 386-88, (1990).
Shimizu et al., "Degradation of human brain natriuretic peptide (BNP) by contact activation of blood coagulation system." *Clin. Chem. Acta* 305: 181-6, (2001).
Shimizu et al., "Molecular forms of human brain natriuretic peptide in plasma." *Clin. Chem. Acta* 316: 129-35, (2002).
Smith et al., "Delayed metabolism of human brain natriuretic peptide reflects resistance to neutral endopeptidase." *J. Endocrinol.* 167: 239-46, (2000).
Tateyama et al., "Concentrations and molecular forms of human brain natriuretic peptide in plasma." *Biochem. Biophys. Res. Commun.* 185:760-7, (1992).
Trindade and Rouleau, "Vasopeptidase inhibitors: potential role in the treatment of heart failure." *Heart Fail. Monit.* 2: 2-7, (2001).
Troughton et al., "Treatment of heart failure guided by plasma aminoterminal brain natriuretic peptide (N-BNP) concentrations." *Lancet* 355: 1126-30, (2000).
Van Veldhuisen et al., "High-Versus low-dose ACE inhibition in chronic heart failure: A double-blind, placebo-controlled study of Imidapril." *J. Am. Coll. Cardiol.* 32: 1811-8 (1998).
Venugopal, "Cardiac natriuretic peptides—hope or hype?" *J. Clin. Pharm. Ther.* 26: 15-31, (2001).
Ward et al., "Binding activities of a repertoire of single immunoglobulin variable domains secreted from *Escherichia coli*." *Nature* 341:544-546, (1989).
Wilson, "Simplified conjugation chemistry for coupling peptides to F(ab') fragments; autologous red cell agglutination assay for HIV-1 antibodies." *J. Immunol. Methods* 175:267-273, (1994).
Wright et al., "Proteinchip® surface enhanced laser desorption/ionization (SELDI) mass spectrometry: a novel protein biochip technology for detection of prostate cancer biomarkers in complex protein mixtures." *Prostate Cancer and Prostatic Diseases* 2: 264-76, (1999).
Yarmush, "Coupling of antibody-binding fragments to solid-phase supports: site-directed binding of F(ab')$_2$ fragments." *J. Biochem. Biophys. Methods* 25:85-97, (1992).
Baker, In Biomarkers we trust?, Nature Biotechnology, 23(3): 297-304, 2005.
Bast et al., Translational crossroads for biomarkers, Clin Cancer Research, 11(17): 6103-6108, 2005.
Corti et al., Vasopeptidase inhibitors: A New therapeutic concept in cardiovascular disease?, Circulation, 104:1856-1862, 2001.
European Search Report for EP Application No. 04781634.3-2401.
Jones et al., Hematopoietic stimulation by a dipeptidyl peptidase inhibitor reveals a novel regulatory mechanism and therapeutic treatment for blood cell deficiencies. Blood, 102(5): 1641-1648, 2003.
LaBaer, So, you want to look for biomarkers (Introduction to the special biomarkers issue), Journal of Proteome Research, 4:1053-1059, 2005.

Walther et al., Biochemical analysis of neutral endopeptidase activity reveals independent catabolism of atrial and brain natriuretic peptide. Biol. Chem., 385: 179-184, Feb. 2004.

International Search Report for PCT Application PCT/US2002/11441.

European Search Report dated May 2, 2008 from EP Application No. EP05797663.

Antman, et al. Cardiac-specific Troponin I Levels to Predict the Risk of Mortality in Patients with Acute Coronary Syndromes. The New England Journal of Medicine. 1996; 335(18):1342-1349.

Arakawa, et al. Plasma Brain Natriuretic Peptide Concentrations Predict Survival After Acute Myocardial Infarction. J. Am. Coll. Cardiol. Jun. 1996; 27(7):1656-61.

Asano, et al. Complementary DNA cloning, tissue distribution, and synthesis of canine brain natriuretic peptide. Am J Vet Res. Jul. 1999;60(7):860-4.

Baker, et al. Serum Metalioproteinases and their inhibitors: markers for malignant potential. Br. J. Cancer 1994;70:506-512.

Berger, et al. 8-Anilinoimidazo[4,5-g]quinoline-7-carbonitriles as Src kinase inhibitors. Bioorg Med Chem Lett. Oct. 7, 2002;12(19):2761-5.

European Search Report dated Sep. 19, 2007 for EP Application No. EP06002477.5.

Hassan, et al. Non-viable myocardium, documented by TL-201 SPECT, is a main determinant of the increase in the secretion of cardiac natriuretic peptides. Medecine Nucleaire. 2000; 24(6):301-310 (Database EMBASE Accession No. 2001129199 and English language translation).

Hoogenboom, H. R. Designing and optimizing library selection strategies for generating high-affinity antibodies. Trends Biotechnol. Feb. 1997;15(2):62-70.

International Search Report dated Oct. 17, 2005 from PCT Application No. US05/32287.

International Search Report dated Feb. 27, 2003 for PCT Application No. US2002/14219.

Katus, et al. Diagnostic Efficency of Troponin T Measurements in Acute Myocardial Infaction. Circulation. 1991;83:902-912.

Newby, et al. Bedside Multimarker Testing for Risk Stratification in Chest Pain Units; The Chest Pain Evaluation by Creatine Kinase-MB, Myoglobin and Troponin I (Checkmate) Study. Circulation. Apr. 10, 2001; 103: 1832-1837.

Singh, et al. Clinical profile of Q-wave and Non-Q wave myocardial infarction. Journal of Indian Academy of Clinical Medicine. 2004;5(1):24-26.

Stedman's Medical Dictionary, 26th Edition, definition of "infarct." 1995.

Supplementary European Search Report dated Aug. 9, 2006 for EP Application No. 04760003.6.

Supplementary European Search Report dated Sep. 19, 2005 for EP Application No. 02734211.2.

Tateishi, et al. Transient Increase in Plasma Brain (B-Type) Natriuretic Peptide After Percutaneous-Transluminal Coronary Angioplasty. Clinical Cardiology. 2000; 23:776-780.

Theroux, et al. Acute Coronary Syndromes: Unstable angina and non-Q-wave myocardial infarction. Circulation. 1998; 97:1195-1206.

University of Pennsylvania Health System, Glossary. Acute Myocardial Infarction. Available at: http://pennhealth.com/cardiac/pcc_glossary.html Accessed Jan. 30, 2007.

Wei, et al. Natriuretic peptide system in human heart failure. Circulation, Sep. 1993;88(3):1004-9.

Boomsma, et al. Plasma A- and B-type Natriurectic Peptides: Physiology; Methodology and Clinical Use. Cardiovascular Research. 2001; 51: 442-449.

Clerico, et al. Circulating levels of cardiac natriuretic peptides (ANP and BNP) measured by highly sensitive and specific immunoradiometric assays in normal subjects and in patients with different degrees of heart failure. J Endocrinol Invest. 1998 Mar;21(3):170-9.

Hammerer-Lercher et al. Cardiac natriuretic peptides: new laboratory parameters in heart failure patients. Clin Lab. 2001; 47(5-6):265-77.

Hammerer-Lercher et al. Head-to-Head Comparison of N-terminal Pro-brain Natriuretic Peptide, Brain Natiuretic Peptide and N-terminal Pro-atrial Natriuretic Peptide in Diagnosing Left Venticular Dysfunction. Clinica Chimica Acta. 2001; 310:193-197.

Heeschen, et al. Troponin concentrations for stratification of patients with acute coronary syndromes in relation to therapeutic efficacy of tirofiban, PRISM Study Investigators. Platelet Receptor Inhibition in Ischemic Syndrome Management. The Lancet. 1999;354(9192): 1757-62.

Horio et al. Serial Changes in Atrial and Brian Natriuretic Peptides In Patients with Acute Myocardinal Infraction Treated with Early Coronary Angioplasty. American Heart Journal. 1993 Aug; 126(2):293-299.

Jabor, et al. Natriuretic Peptides can predict cardiac failure. Klinicka Biochemie a Metalbolismus. 1999; 7(1): 44-48. (in Chzec with English abstract).

Kelly, et al. Are Natiuretic Peptides Clinically Useful as Markers of Heart Failure? Ann. Clin. Biochem. 2001; 38:94-102.

Kucher, et al. Low pro-brain natiuretic peptide levels predict benign clinical outcome in acute pulmonary embolism. Circulation. 2003 Apr. 1;107(12):1576-8.

Lainchbury, et al. Brain Natiuretic Peptide and N-Terminal Brain Natriuretic Peptide in the Diagnosis of Heart Failure in Patients With Acute Shortness of Breath. J. Am. Coll. Cardiol. Aug. 20, 2003;42(4):728-35.

McGeoch, et al. Plasma Brain Natriuretic Peptide After Long-Term Treatment for Heart Failure in General Practice, The European Journal of Heary Failure, 2002, pp. 479-483, vol. 4, Elsevier Science B.V.

Nagaya et al., Plasma Brain natriuretic Peptide asa Prognostic Indicator in Patients with Primary Pulmonary Hypertension, Circulation, Aug. 22, 2000, pp. 865-870, vol. 102.

Omland et al., N-Terminal Pro-brain Natriuretic Peptide is An Independent Predictor of Survival in Patients with Non-ST-Segment Elevation Acute Coronary Syndromes: a TIMI 11B Substudy, Journal of the European Society of Cardiology, Sep. 22, 2001; 22:608.

Qi, et al. Effects of different peptide fragment derived from proadrenomedulin on gene expression of adrenomedulin gene. Peptides. 2002;23: 1141-1147.

Richards et al., Plasma N-Terminal Pro-Brain Natriuretic Peptide and Adrenomedullin; New Neurohormonal Predictors of Left Venticular Functionand Prognosis After Myocardial Infraction, May 19, 1998;97:1921-1929.

Safley, et al. The emerging role of brain natriuretic peptide in the management of acute and chronic heart failure in outpatients. Heart Fail Monit. 2003;4(1):13-20.

Talwar at al. Plasma N-terminal Pro-Brain Natriuretic Peptide and Cardiotrophin 1 are raised in Unstable Angina. Heart, 2000; 84:421-424.

Talwar et al., Profile of Plasma N-Terminal proBNP Following Acute Myocardial Infraction; Correlation with left Ventricular Systolic Dysfunction, Eur. Heart J., Sep. 2000; 21:18:1514-1521.

Tang, et al. B-Type Natriuretic Peptide: A critical review. CHF. 2007;12:48-52.

Tao, et al. Studies of aglycosylated chimeric mouse-human IgG. Role of carbohydrate in the structure and effector functions mediated by the human IgG constant region. J Immunol. Oct. 15, 1989;143(8):2595-601.

Troughton, et al. Plasma B-Type Natriuretic Peptide levels in Systolic Heart Failure, J. Am. Coll. Cardiol., Feb. 4, 2004; Elsevier Inc. 43:3:416-22.

Tsutamoto, et al. Plasma brain natriuretic peptide level as a biochemical marker of morbidity and mortality in patients with asymptomatic or minimally symptomatic left ventricular dysfunction. Comparsion with plasma angiotensin II and endothelin-1. Eur Heart J. Dec. 1999;20(24):1799-807.

Yandle, et al. Brain Natriuretic Peptide - Its Function and Diagnostic Application, Clin. Biochemist, Rev., Feb. 2002; 23:3-21.

Yip, et al. Time course and prognostic value of plasma levels of N-terminal pro-brain natriuretic peptide in patients after ischemic stroke. Circ J. Apr. 2006;70(4):447-52.

* cited by examiner

METHODS AND COMPOSITIONS FOR MEASURING NATRIURETIC PEPTIDES AND USES THEREOF

CROSS-REFERENCE TO RELATED PATENT APPLICATIONS

This application is a Continuation-in-Part of PCT Application No. PCT/US04/26984, filed Aug. 19, 2004, which claims priority to U.S. Provisional Application No. 60/542,086, filed Aug. 20, 2003, and which is a Continuation-in-Part of U.S. application Ser. No. 10/645,874, filed Aug. 20, 2003, which is a Continuation-in-Part of U.S. application Ser. No. 10/419,059, filed Apr. 17, 2003, which is a Continuation-in-Part of U.S. application Ser. No. 09/835,298, filed Apr. 11, 2002, and which is a Continuation-in-Part of PCT Application No. PCT/US02/26604, filed Aug. 20, 2002, which claims priority to U.S. Provisional Application No. 60/313,775, filed Aug. 20, 2004, and 60/334,964, filed Nov. 30, 2001, and 60/346,485, filed Jan. 2, 2002, U.S. application Ser. No. 10/419,059 is also a Continuation-in-Part of U.S. application Ser. No. 10/139,086, filed May 4, 2002, which claims priority to U.S. Provisional Application No. 60/288,871, filed May 4, 2001, and 60/315,642, filed Aug. 28, 2001, from each of which priority is claimed, and each of which is fully incorporated by reference herein.

FIELD OF THE INVENTION

The present invention relates to medical diagnostics and therapeutics.

BACKGROUND OF THE INVENTION

The following discussion of the background of the invention is merely provided to aid the reader in understanding the invention and is not admitted to describe or constitute prior art to the present invention.

Natriuretic peptides are a group of naturally occurring substances that act in the body to oppose the activity of the renin-angiotensin system. There are three major natriuretic peptides: atrial natriuretic peptide (ANP), which is synthesized in the atria; brain-type natriuretic peptide (BNP), which is synthesized in the ventricles; and C-type natriuretic peptide (CNP), which is synthesized in the brain.

Mature human B-type natriuretic peptide (BNP) (also called brain-type natriuretic peptide and $BNP_{77-108}$) is a 32 amino acid, 4 kDa biologically active peptide that is involved in the natriuresis system to regulate blood pressure and fluid balance (Bonow, R. O., *Circulation* 93: 1946-1950, 1996). The mature BNP hormone is generated by proteolytic cleavage of a 108-amino acid precursor molecule, referred to herein as "pro-BNP" (or $BNP_{1-108}$). Cleavage generates a 76-amino acid N-terminal peptide, referred to as "NT pro BNP" (or $BNP_{1-76}$) and the 32-amino acid mature $BNP_{77-108}$ hormone. It has been suggested that each of these species—NT pro-BNP, BNP-32, and the pre-pro-BNP—can circulate in human plasma (Tateyama et al., *Biochem. Biophys. Res. Commun.* 185: 760-7, 1992; Hunt et al., *Biochem. Biophys. Res. Commun.* 214:1175-83, 1995).

BNP is released in response to ventricular stretch, and will cause vasorelaxation, inhibition of aldosterone secretion in the adrenal cortex, and inhibition of renin secretion in the kidney. BNP release will cause natriuresis and a reduction in intravascular volume, effects amplified by the antagonism of antidiuretic hormone (ADH). Increased blood levels of BNP have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; and WO 03/016910, each of which is hereby incorporated in its entirety, including all tables, figures, and claims. For example, BNP, which is synthesized in the cardiac ventricles and correlates with left ventricular pressure, amount of dyspnea, and the state of neurohormonal modulation, makes this peptide the first potential marker for heart failure. Measurement of plasma BNP concentration is evolving as a very efficient and cost effective mass screening technique for identifying patients with various cardiac abnormalities regardless of etiology and degree of LV systolic dysfunction that can potentially develop into obvious heart failure and carry a high risk of a cardiovascular event. Finding a simple blood test that would aid in the diagnosis and management of patients with CHF clearly would have a favorable impact on the staggering costs associated with the disease.

Removal of the natriuretic peptides from the circulation is affected mainly by binding to clearance receptors and enzymatic degradation in the circulation. See, e.g., Cho et al., *Heart Dis.* 1: 305-28, 1999; Smith et al., *J. Endocrinol.* 167: 239-46, 2000. Additionally, human pro-BNP is reported to be processed in serum such that circulating pre-pro-BNP is unlikely to be the intact 108 amino acid form. Hunt et al., *Peptides* 18: 1475-81, 1997. Degradation of the natriuretic peptides is believed mediated by neutral endopeptidase. For example, Norman et al. (*Biochem. Biophys. Res. Commun.* 28: 175: 22-30, 1991) report that neutral endopeptidase can cleave human BNP between residues 2 and 3, between residues 4 and 5, and between residues 17 and 18. Additionally, Knecht et al. (*Life Sci.* 71: 2701-12, 2002) report that renal neutral endopeptidase is upregulated in heart failure, a condition where natriuretic peptide levels are increased. For this reason, neutral endopeptidase has been targeted for inhibition in treatment of cardiovascular disease. See, e.g., Corti et al., *Circulation* 104: 1856-62, 2001.

Confusion over the stability of the natriuretic peptides, particularly in blood-derived samples (e.g., serum, plasma, whole blood) has been reported. ANP is reported to be a better substrate for neutral endopeptidase than is BNP. Similarly, Shimizu et al. (*Clin. Chem. Acta* 305: 181-6, 2001), Gobinet-Georges et al. (*Clin. Chem. Lab. Med.* 38: 519-23, 2000) and Murdoch et al. (*Heart* 78: 594-7, 1997) report that BNP is stable in certain blood-derived samples or when blood is collected under certain conditions. A more recent report by Shimizu et al. (*Clin. Chem. Acta* 316: 129-35, 2002) indicates that 94% of BNP in whole blood was a digested form in which 2 amino terminal residues had been removed; and that BNP in plasma was degraded to a number of unidentified forms.

BRIEF SUMMARY OF THE INVENTION

The present invention relates in part to compositions and methods designed to determine the presence or amount of one or more natriuretic peptides, or their fragments, in a sample. The degradation of natriuretic peptides is an ongoing process that may be a function of, inter alia, the elapsed time between onset of an event triggering natriuretic peptide release into the tissues and the time the sample is obtained or analyzed; the quantity of proteolytic enzymes present; etc. This degradation can produce circulating amounts of natriuretic peptides lost one or more amino acids.

Failure to consider this degradation when designing an assay for one or more natriuretic peptides may result in an assay that detects several forms of a natriuretic peptide.

Because the various forms may yield independent results related to the physiologic state of the subject, and because upregulated proteolytic enzymes in diseased subjects may lead to particularly large pools of fragments in the subjects of potentially the greatest interest, the compositions and methods described herein may provide improved diagnostic and prognostic information to the artisan.

The methods and compositions described herein can meet the need in the art for rapid, sensitive and specific diagnostic assay to be used in the diagnosis and differentiation of various cardiovascular diseases, including stroke, congestive heart failure (CHF), cardiac ischemia, systemic hypertension, and/or acute myocardial infarction. Moreover, the methods and compositions of the present invention can also be used to facilitate the treatment of patients and the development of additional diagnostic and/or prognostic indicators and indicator panels.

In a related object, the present invention relates to methods for detecting the presence or amount of one or more natriuretic peptides in a sample, comprising performing an assay that is sensitive to degradation as described above. Molecules excluded from detection by such assays are referred to as "non-target" natriuretic peptides.

In a first object, the present invention relates to methods for detecting the presence or amount of one or more natriuretic peptide related species (as defined hereinafter) in a sample, comprising performing an assay that is "insensitive" or "sensitive" to degradation at the amino and/or carboxyl terminus of a particular polypeptide of interest, as described below.

In a related object of the invention, the present invention relates to methods for the diagnosis and/or prognosis of a subject, comprising performing an assay that detects the presence or amount of BNP, pro-BNP, and/or one or more fragments related thereto, in a sample obtained from the subject, and relating the assay result to a particular diagnosis and/or prognosis. In preferred embodiments, the subject is suspected of having or has been diagnosed as having one or more cardiovascular conditions as defined herein. The materials and procedures described herein can preferably be used to identify those patients suffering from an acute coronary syndrome, and/or that are at risk for one or more serious adverse outcomes, including the risk of death, resulting from acute coronary syndromes.

In certain embodiments, such assays are designed to be "insensitive" to degradation of the amino and/or carboxyl terminus of pro-BNP. For example, antibodies may be selected to bind to particular regions of the $BNP_{1-108}$ molecule, such that target molecules derived by removal of between 0 and 1, 2, 3, 4, 5, 6, 7, 8, 9, or 10 residues from the amino terminus of $BNP_{1-108}$, and/or removal of between 0 and 1, 2, 3, 4, 5, 6, 7, 8, 9, or 10 residues from the carboxyl terminus of $BNP_{1-108}$, generate a substantially equivalent assay response. In related embodiments, such assays are designed to be "insensitive" to degradation of the amino and/or carboxyl terminus of BNP. For example, antibodies may be selected to bind to particular regions of the $BNP_{77-108}$ molecule, such that target molecules derived by removal of between 0 and 1, 2, 3, 4, 5, 6, 7, 8, or 9 residues from the amino terminus of $BNP_{77-108}$, and/or removal of between 0 and 1, 2, 3, 4, or 5 residues from the carboxyl terminus of $BNP_{77-108}$, generate a substantially equivalent assay response.

Assay responses that are within a factor of 5, and most preferably within a factor of 2, for equimolar amounts of a plurality of target molecules are said to be "insensitive" with respect to those target molecules. Molecules providing assay responses in such assays that are not within a factor of 5, and most preferably not within a factor of 10, for equimolar amounts of the target molecules are referred to as "non-target" natriuretic peptides.

Preferably, however, assays are designed to be "sensitive" to degradation of the amino and/or carboxyl terminus of BNP or pro-BNP. Thus, assays may be configured such that intact $BNP_{1-108}$, or pro-BNP fragments having an intact amino terminus, are detected with at least a 5-fold, and most preferably a 10-fold or more, reduction in signal relative to equimolar amounts of those pro-BNP fragments in which the amino terminus has lost 1, 2, 3, 4, 5, 6, 7, 8, 9, 10, or more residues. In the alternative, assays may be configured such that pro-BNP fragments in which the amino terminus has lost 1, 2, 3, 4, 5, 6, 7, 8, 9, 10, or more residues are detected with at least a 5-fold, and most preferably a 10-fold or more, reduction in signal relative to equimolar amounts of intact $BNP_{1-108}$ or pro-BNP fragments having an intact amino terminus.

In related embodiments, assays may be configured such that intact $BNP_{77-108}$, or $BNP_{77-108}$ fragments having an intact amino terminus, are detected with at least a 5-fold, and most preferably a 10-fold or more, reduction in signal relative to equimolar amounts of intact $BNP_{77-108}$ or $BNP_{77-108}$ fragments in which the amino terminus has lost 1, 2, 3, 4, 5, 6, 7, 8, 9, or more residues. In the alternative, assays may be configured such that intact $BNP_{77-108}$ or $BNP_{77-108}$ fragments in which the amino terminus has lost 1, 2, 3, 4, 5, 6, 7, 8, 9, or more residues are detected with at least a 5-fold, and most preferably a 10-fold or more, reduction in signal relative to equimolar amounts of those $BNP_{77-108}$ fragments having an intact amino terminus.

Similarly, assays may be configured to be sensitive to degradation of the carboxyl terminus. Thus, assays may be configured such that intact $BNP_{1-108}$, or pro-BNP fragments having an intact carboxyl terminus, are detected with at least a 5-fold reduction in signal relative to equimolar amounts of those pro-BNP fragments in which the carboxyl terminus has lost 1, 2, 3, 4, 5, 6, 7, 8, 9, 10, or more residues. In the alternative, assays may be configured such that pro-BNP fragments in which the carboxyl terminus has lost 1, 2, 3, 4, 5, 6, 7, 8, 9, 10, or more residues are detected with at least a 5-fold reduction in signal relative to equimolar amounts of intact $BNP_{1-108}$ or pro-BNP fragments having an intact carboxyl terminus. Likewise, assays may be configured such that intact $BNP_{77-108}$, or $BNP_{77-108}$ fragments having an intact carboxyl terminus, are detected with at least a 5-fold reduction in signal relative to equimolar amounts of those $BNP_{77-108}$ fragments in which the carboxyl terminus has lost 1, 2, 3, 4, 5, 6, or more residues. In the alternative, assays may be configured such that $BNP_{77-108}$ fragments in which the carboxyl terminus has lost 1, 2, 3, 4, 5, 6, or more residues are detected with at least a 5-fold reduction in signal relative to equimolar amounts of intact $BNP_{77-108}$ or $BNP_{77-108}$ fragments having an intact carboxyl terminus.

In various preferred embodiments, the assays of the present invention are configured to detect the presence or amount in a sample of $BNP_{1-108}$, and one or more pro-BNP related fragments selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$, in an insensitive manner. In other preferred embodiments, however, the assays of the present invention are configured provide a signal that is insensitive to one or more pro-BNP related fragments selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$, but that exhibit at least a 5-fold reduction in signal from, more preferably a 10-fold reduction in signal from, and most preferably do not appreciably detect, an equimolar amount of $BNP_{1-108}$. In yet other preferred embodiments, the assays of the present invention are configured provide a signal from $BNP_{1-108}$, but exhibit at least a 5-fold reduction in signal from, and preferably do not appreciably detect, an equimolar amount of one or more pro-BNP related fragments selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$.

In various other preferred embodiments, the assays of the present invention are configured to detect the presence or amount in a sample of $BNP_{77-108}$, and one or more BNP related fragments selected from the group consisting of $BNP_{79-108}$, $BNP_{81-108}$, $BNP_{83-108}$, $BNP_{77-106}$, $BNP_{79-106}$, $BNP_{81-106}$, and $BNP_{83-106}$, in an insensitive manner. In other preferred embodiments, however, the assays of the present invention are configured provide a signal that is insensitive to one or more BNP related fragments selected from the group consisting of $BNP_{79-108}$, $BNP_{81-108}$, $BNP_{83-108}$, $BNP_{77-106}$, $BNP_{79-106}$, $BNP_{81-106}$, and $BNP_{83-106}$, but that exhibit at least a 5-fold reduction in signal from, more preferably a 10-fold reduction in signal from, and most preferably do not appreciably detect, an equimolar amount of $BNP_{77-108}$. In yet other preferred embodiments, the assays of the present invention are configured provide a signal from $BNP_{77-108}$, but exhibit at least a 5-fold reduction in signal from, and preferably do not appreciably detect, an equimolar amount of one or more BNP related fragments selected from the group consisting of $BNP_{79-108}$, $BNP_{81-108}$, $BNP_{83-108}$, $BNP_{77-106}$, $BNP_{79-106}$, $BNP_{81-106}$, and $BNP_{83-106}$.

An assay does not "appreciably detect" a second group of polypeptides if a signal related to binding of the first group of polypeptides may be obtained, but no signal above background is obtained from an equimolar amount of the second group of polypeptides under such assay conditions.

As described hereinafter, such assays may be designed in a variety of ways known to those of skill in the art. Preferred assays are immunoassays, although other methods are well known to those skilled in the art (for example, the use of biosensors comprising an integrated analyte receptor and transducer, or the use of natural receptors for natriuretic peptides that are known in the art). Any suitable immunoassay may be utilized, for example, assays which directly detect analyte binding (e.g., by ellipsometric detection), enzyme-linked immunoassays (ELISA), radioimmunoassays (RIAs), competitive binding assays, sandwich immunoassays, and the like. Specific immunological binding of the antibody or receptor to the one or more natriuretic peptide fragments can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. Antibodies attached to a second molecule, such as a detectable label, are referred to herein as "antibody conjugates." The skilled artisan will also understand that natural receptors for the natriuretic peptides exist, and that these receptors may also be used in a manner akin to antibodies in providing binding assays.

Immunoassays may be formulated using one or more antibodies selected to bind to an epitope that is partially or completely absent from non-target fragments of the natriuretic peptide as compared to the target natriuretic peptide. For example, in a sandwich assay, if an antibody bound to a solid phase is selected to bind preferentially to the N-terminal portion of the molecule, and a labeled antibody is selected to bind to the C-terminal portion of the molecule, only those molecules that contain both the N- and C-terminal portions of the molecule will be detected in the assay. Alternatively, both the solid phase and labeled antibodies may be selected to bind to the N-terminal portion of the molecule.

The skilled artisan will understand that cleavage of the natriuretic peptide may remove all of the epitope to which one antibody binds (e.g., the antibody binds to the native N-terminal region), while uncovering new epitopes (e.g., the antibody binds to the new N-terminal region upon loss of one or more native N-terminal residues). Alternatively, an epitope may be formed from portions of the natriuretic peptide that are not contiguous in the linear sequence of the molecule, but that are associated in 3-dimensional space in solution, so that epitope comprises more than the described amino acid residues, but removal of the region described amino acid residues results in reduced binding of the antibody, and hence a loss of signal in the assay.

The immunoassays of the present invention are preferably designed to distinguish various natriuretic peptides. An immunoassay is said to "distinguish" between a first group of polypeptides and a second group of polypeptides if the immunoassay provides a signal related to binding of the first group of polypeptides that is at least a factor of 5 greater than a signal obtained from an equal number of molecules of the second group of polypeptides under the same assay conditions, when the assay is performed at no more than twice the amount of the first group of polypeptides necessary to obtain a maximum signal. More preferably, the signal is at least a factor of 10 greater, even more preferably at least a factor of 20 greater, and most preferably at least a factor of 50 greater, at least a factor of 100 greater, or more under such assay conditions.

In another object, the present invention relates to antibodies that are either "insensitive" or "sensitive" to the degradation state of $BNP_{77-108}$ or $BNP_{1-108}$ at the amino and/or carboxyl terminus. Antibodies are said to be "insensitive" with respect to a first target polypeptide and a second target polypeptide if the antibody exhibits substantially identical binding to the two target polypeptides. Antibodies that are not "insensitive" with respect to two polypeptides are said to be "sensitive" with respect to the polypeptides.

The term "substantially identical binding" refers to an antibody that, when used in an assay, provides signals that are within a factor of 5, and most preferably a factor of 2, for equimolar amounts of two target polypeptides. A factor of 1 indicates that the signals are equal; that signals are within a factor of 2 indicates that one signal is less than or equal to the other signal ×2. Preferably, antibodies exhibiting substantially identical binding provide signals that are within a factor of about 1.75, more preferably within a factor of about 1.5, still more preferably within a factor of about 1.25, and most preferably within a factor of about 1.1 to 1.

Such antibodies may also have "substantially identical affinity" with respect to a first target polypeptide and a second target polypeptide, meaning an affinity that is within a factor of 5, and most preferably a factor of 2, for the two target polypeptides. A factor of 1 indicates that the affinities are equal; that affinities are within a factor of 2 indicates that one affinity is less than or equal to the other signal ×2. Preferably, antibodies exhibiting substantially identical binding provide affinities that are within a factor of about 1.75, more preferably within a factor of about 1.5, still more preferably within a factor of about 1.25, and most preferably within a factor of about 1.1 to 1.

Certain preferred antibodies of the invention are insensitive with respect to at least two polypeptides selected from the group consisting of $BNP_{1-108}$, $BNP_{3-108}$, $BNP_{5-108}$, $BNP_{7-108}$, $BNP_{1-106}$, $BNP_{3-106}$, $BNP_{5-106}$, and $BNP_{7-106}$.

Particularly preferred antibodies of the invention are insensitive with respect to $BNP_{1-108}$ and pro-BNP fragments having lost two amino terminal residues (e.g., $BNP_{3-108}$, $BNP_{3-106}$, etc.), such that the antibodies exhibit substantially identical binding to $BNP_{1-108}$ and pro-BNP fragments having lost two amino terminal residues.

Certain other preferred antibodies, however, are sensitive with respect to at least two polypeptides selected from the group consisting of $BNP_{77-108}$, $BNP_{79-108}$, $BNP_{81-108}$, $BNP_{83-108}$, $BNP_{77-106}$, $BNP_{79-106}$, $BNP_{81-106}$, and $BNP_{83-106}$; or at least two polypeptides selected from the group consisting of $BNP_{1-108}$, $BNP_{3-108}$, $BNP_{5-108}$, $BNP_{7-108}$, $BNP_{1-106}$, $BNP_{3-106}$, $BNP_{5-106}$, and $BNP_{7-106}$. Particularly preferred antibodies of the invention are sensitive with respect to $BNP_{1-108}$ and pro-BNP fragments having lost two amino terminal residues (e.g., $BNP_{3-108}$, $BNP_{3-106}$, etc.). Such a sensitive antibody may bind, for example, $BNP_{1-108}$, but show a reduced assay signal for equimolar amounts of $BNP_{3-108}$. Alternatively, such a sensitive antibody may bind, for example, $BNP_{3-108}$, but show a reduced assay signal for equimolar amounts of $BNP_{1-108}$. Other particularly preferred antibodies of the invention are sensitive with respect to $BNP_{77-108}$ and BNP fragments having lost two amino terminal residues (e.g., $BNP_{79-108}$, $BNP_{79-106}$, etc.). Such a sensitive antibody may bind, for example, $BNP_{77-108}$, but show a reduced assay signal for equimolar amounts of $BNP_{79-108}$. Alternatively, such a sensitive antibody may bind, for example, $BNP_{79-108}$, but show a reduced assay signal for equimolar amounts of $BNP_{77-108}$.

A signal from an immunoassay is said to "depend upon binding to an antibody" if the antibody participates in formation of a complex necessary to generate the signal. For example, in a sandwich immunoassay formulated using a solid phase antibody and a second antibody conjugate, each of which must bind to an analyte to form the sandwich, each of the solid phase antibody and second antibody participate in formation of the complex necessary to generate the signal. In a competitive immunoassay where a single antibody is used, and an analyte competes with an analyte conjugate for binding, the single antibody participates in formation of the complex necessary to generate the signal. The skilled artisan will understand that numerous additional immunoassay formulations may be provided.

It will be apparent to the artisan that various combinations of sensitive and/or insensitive antibodies and assays as described herein may be used in a variety of assat formats in diagnostic and/or prognostic methods. For example, an assay may be configured with the antibody that binds to a first set of polypeptide(s), and a second assay may be configured with the antibody that binds to a second set of polypeptide(s), to provide a ratio of of the two groups of polypeptides. Likewise, such an assay may be configured with the antibody that binds to a first set of polypeptide(s), and a second assay may be configured with the antibody that binds to the second set of polypeptide(s), and the results summed to provide a total amount of the two groups of polypeptides. As described hereinafter, devices may be provided that perform multiple assays on the same sample.

When used in diagnostic and/or prognostic methods, the assays and antibodies described herein that are sensitive and/or insensitive for various natriuretic peptide related species may also be used in providing a plurality of markers, comprising 2, 3, 4, 5, 6, 7, 8, 9, 10, 15, 20, or more individual markers, which may be combined into a marker panel. Suitable markers for use in combination with the assays described herein include the various "markers related to blood pressure regulation," "markers related to coagulation and hemostasis," "markers related to inflammation," "markers related to vascular tissue," and "markers related to apoptosis" as described in PCT/US03/41453, filed Dec. 23, 2003, which is hereby incorporated by reference in its entirety. Particularly preferred markers include caspase-3, thrombus precursor protein, creatine kinase-MB, free and complexed cardiac troponin I, free and complexed cardiac troponin T, free cardiac troponin I, free cardiac troponin T, complexed cardiac troponin I, complexed cardiac troponin T, myoglobin, B-type natriuretic peptide, NT-proBNP, C-reactive protein, D-dimer, myeloperoxidase, and markers related thereto.

In yet other embodiments, multiple determinations using the assays described herein can be made, and a temporal change in the markers can be used for diagnosis and/or prognosis. For example, one or more polypeptides may be determined at an initial time, and again at a second time, and the change (or lack thereof) in the polypeptide level(s) over time determined. In such embodiments, an increase in the polypeptide(s) from the initial time to the second time may be diagnostic of a particular disease underlying one or more symptoms, a particular prognosis, etc. Likewise, a decrease from the initial time to the second time may be indicative of a particular disease underlying one or more symptoms, a particular prognosis, etc. Temporal changes in one or more markers may also be used together with single time point marker levels to increase the discriminating power of marker panels.

Thus, in another object, the present invention relates to assay devices configured and arranged to perform the described assays. Devices for performing the assays described herein preferably contain a plurality of discrete, independently addressable locations, or "diagnostic zones," each of which is related to a particular analyte or set of analytes of interest, one or more of which is a natriuretic peptide. For example, each of a plurality of discrete zones may comprise a receptor (e.g., an antibody) for binding a different analyte. Following reaction of a sample with the devices, a signal is generated from the diagnostic zone(s), which may then be correlated to the presence or amount of the peptide of interest.

In still another object, the present invention relates to methods for selecting one or more sensitive and/or insensitive antibodies. These methods comprise screening antibody preparations for sensitivity (or the lack thereof) using methods well known in the art. Exemplary screening methods are described hereinafter. Once selected, such antibodies may be used in the methods described herein for measurement of natriuretic peptides.

Certain preferred selection methods identify one or more antibodies that are insensitive with respect to at least two polypeptides selected from the group consisting of $BNP_{77-108}$, $BNP_{79-108}$, $BNP_{81-108}$, $BNP_{83-108}$, $BNP_{77-106}$, $BNP_{79-106}$, $BNP_{81-106}$, and $BNP_{83-106}$; or at least two polypeptides selected from the group consisting of $BNP_{1-108}$, $BNP_{3-108}$, $BNP_{5-108}$, $BNP_{7-108}$, $BNP_{1-106}$, $BNP_{3-106}$, $BNP_{5-106}$, and $BNP_{7-106}$.

Particularly preferred selection methods identify one or more antibodies that are insensitive with respect to $BNP_{1-108}$ and pro-BNP fragments having lost two amino terminal residues (e.g., $BNP_{3-108}$, $BNP_{3-106}$, etc.), such that the antibodies exhibit substantially identical binding to $BNP_{1-108}$ and pro-BNP fragments having lost two amino terminal residues. Other particularly preferred selection methods identify one or more antibodies that are insensitive with respect to $BNP_{77-108}$ and BNP fragment shaving lost two amino terminal residues (e.g., $BNP_{79-108}$, $BNP_{79-106}$, etc.), such that the antibodies exhibit substantially identical binding to $BNP_{79-108}$ and BNP fragments having lost two amino terminal residues.

Certain other preferred selection methods identify one or more antibodies that are sensitive with respect to at least two polypeptides selected from the group consisting of $BNP_{77-108}$, $BNP_{79-108}$, $BNP_{81-108}$, $BNP_{83-108}$, $BNP_{77-106}$, $BNP_{79-106}$, $BNP_{81-106}$, and $BNP_{83-106}$; or at least two polypeptides selected from the group consisting of $BNP_{1-108}$, $BNP_{3-108}$, $BNP_{5-108}$, $BNP_{7-108}$, $BNP_{1-106}$, $BNP_{3-106}$, $BNP_{5-106}$, and $BNP_{7-106}$. Particularly preferred selection methods identify one or more antibodies that are sensitive with respect to $BNP_{1-108}$ and pro-BNP fragments having lost two amino terminal residues (e.g., $BNP_{3-108}$, $BNP_{3-106}$, etc.). Such a sensitive antibody may bind, for example, $BNP_{1-108}$, but show a reduced assay signal for equimolar amounts of $BNP_{3-108}$. Alternatively, such a sensitive antibody may bind, for example, $BNP_{3-108}$, but show a reduced assay signal for equimolar amounts of $BNP_{1-108}$. Other particularly preferred selection methods identify one or more antibodies that are sensitive with respect to $BNP_{77-108}$ and BNP fragments having lost two amino terminal residues (e.g., $BNP_{79-108}$, $BNP_{79-106}$, etc.). Such a sensitive antibody may bind, for example, $BNP_{77-108}$, but show a reduced assay signal for equimolar amounts of $BNP_{79-108}$. Alternatively, such a sensitive antibody may bind, for example, $BNP_{79-108}$, but show a reduced assay signal for equimolar amounts of $BNP_{77-108}$.

In another object, one or more antibodies and/or antibody conjugates of the present invention may be provided as kits for determining the presence or amount of natriuretic peptide(s). These kits preferably comprise devices and reagents for performing at least one assay as described herein on a test sample. Such kits preferably contain sufficient reagents to perform one or more such determinations, and/or Food and Drug Administration (FDA)-approved labeling.

In still another object, the invention relates to methods for determining a treatment regimen for use in a patient. The methods preferably comprise determining the presence or amount of one or more natriuretic peptide(s) by the methods described herein, and relating this presence or amount to a disease or prognostic state. As discussed herein, diagnosis and differentiation of various cardiovascular and cerebrovascular diseases, including stroke, congestive heart failure (CHF), cardiac ischemia, systemic hypertension, acute coronary syndrome, and/or acute myocardial infarction may be related to levels of proBNP and its fragments. Once a diagnosis or prognosis is obtained, a treatment regimen is selected to be consistent with that diagnosis.

The summary of the invention described above is non-limiting and other features and advantages of the invention will be apparent from the following detailed description of the invention, and from the claims.

DETAILED DESCRIPTION OF THE INVENTION

The present invention relates in part to methods for distinguishing between various forms of natriuretic peptides, in particular pro-BNP. As described herein, antibodies may be generated that selectively recognize pro-BNP and/or its degradation products, and used in assays. Such assays can provide important diagnostic and prognostic information in the clinical setting.

The term "natriuretic peptide" as used herein refers to members of a group of naturally occurring polypeptide hormones that act in the body to oppose the activity of the renin-angiotensin system, and their biosynthetic precursors and biologically active fragments. There are three major human natriuretic peptides: atrial natriuretic peptide (ANP), which is synthesized in the atria; brain-type natriuretic peptide (BNP), which is synthesized in the ventricles; and C-type natriuretic peptide (CNP), which is synthesized in the brain.

The term "intact pro-BNP" as used herein with regard to human pro-BNP refers to the full length 108-amino acid molecule shown as SEQ ID NO: 1:
HPLGSPGSAS DLETSGLQEQ RNHLQGKLSE LQVEQTSLEP LQESPRPTGV 50
WKSREVATEG IRGHRKMVLY TLRAPR SPKMVQGSGCFGRK MDRISSSSGL 100
GCKVLRRH 108 (SEQ ID NO: 1).

Mature human BNP, or "the BNP natriuretic peptide," or "BNP-32" (shown underlined above) is a 32 amino acid molecule representing amino acids 77-108 of this precursor, which may be referred to as $BNP_{77-108}$. The remaining residues 1-76 are referred to hereinafter as NT-proBNP, or $BNP_{1-76}$.

The sequences pro-BNP from various other species, including pigs (*Sus scrofa*), cows (*Bos Taurus*), domestic dogs (*Canis familiaris*), domestic cats (*Felis catus*), sheep (*Ovis aries*), mice (*Mus musculus*), rats (*Rattus norvegicus*), etc., are known in the art. See, e.g., Liu et al., Gene 292: 183-190, 2002.

The term "fragment" as used herein refers to a polypeptide that comprises at least six contiguous amino acids of a polypeptide from which the fragment is derived, but is less than the complete parent polypeptide. Thus, a fragment of pro-BNP ($BNP_{1-108}$) refers to a polypeptide that comprises at least six contiguous amino acids of $BNP_{1-108}$. In preferred embodiments, a fragment refers to a polypeptide that comprises at least 10 contiguous amino acids of a polypeptide from which the fragment is derived; at least 15 contiguous amino acids of a polypeptide from which the fragment is derived; or at least 20 contiguous amino acids of a polypeptide from which the fragment is derived. Most preferred fragments of pro-BNP contain at least six contiguous amino acids of $BNP_{1-76}$, and at least six contiguous amino acids of $BNP_{77-108}$. Thus, most preferred fragments bridge the NT-proBNP/mature BNP cleavage site.

The term "related fragment" as used herein refers to one or more fragments of a particular polypeptide or its biosynthetic parent that may be detected as a surrogate for the polypeptide itself or as independent markers. $BNP_{77-108}$, $BNP_{1-108}$, $BNP_{3-108}$, $BNP_{5-108}$, $BNP_{7-108}$, $BNP_{1-106}$, $BNP_{3-106}$, $BNP_{5-106}$, $BNP_{7-106}$ and $BNP_{1-76}$ are examples of "BNP-related fragments."

For convenience, a particular natriuretic peptide (or biosynthetic precursor) and fragments derived from that molecule are referred to herein collectively as "related species." Thus, pro-BNP (the biosynthetic precursor) and $BNP_{3-108}$, $BNP_{5-108}$, $BNP_{7-108}$, $BNP_{1-106}$, $BNP_{3-106}$, $BNP_{5-106}$, $BNP_{7-106}$, $BNP_{1-76}$, and $BNP_{77-108}$ are "pro-BNP related species." Similarly, $BNP_{77-108}$ (the mature natriuretic hormone BNP) and $BNP_{79-108}$, $BNP_{81-108}$, $BNP_{83-108}$, $BNP_{79-106}$, $BNP_{81-106}$, and $BNP_{83-106}$ are "BNP related species."

The term "amino terminal degradation" as used herein in reference to natriuretic peptide fragments refers to fragments of a natriuretic peptide formed by removal of one or more amino acids from the amino terminal end of the intact peptide. $BNP_{3-108}$ is an example of amino terminal degradation of pro-BNP due to removal of 2 amino terminal residues. Similarly, $BNP_{79-108}$ is an example of amino terminal degradation of BNP due to removal of 2 amino terminal residues. In preferred embodiments, such a fragment is formed by removal of at least 1, 2, 3, 4, 5, 6, 7, 8, 9, 10, 15, 20, or more amino acids from the amino terminal end of the intact peptide; however, natriuretic peptides may comprise both amino terminal and carboxyl terminal degradation. $BNP_{3-106}$ is an example of such degradation of pro-BNP.

The term "carboxyl terminal degradation" as used herein in reference to natriuretic peptide fragments refers to fragments of a natriuretic peptide formed by removal of one or more amino acids from the carboxyl terminal end of the intact peptide. In preferred embodiments, such a fragment is formed by removal of at least 1, 2, 3, 4, 5, 6, 7, 8, 9, 10, 15, 20, or more amino acids from the amino terminal end of the intact peptide. $BNP_{1-106}$ is an example of carboxyl terminal degradation of pro-BNP.

The term "glycosylated" as used herein in regard to polypeptides refers to polypeptides comprising covalently bound sugar units, often in the form of glycan chains. The individual sugar units are referred to herein as "covalently bound carbohydrate residues." Glycosylation of polypeptides in eukaryotics occurs principally through glycosidic bonds to an asparagine side chain ("N-linked"); through glycosidic bonds to serine or threonine side chains ("O-linked"); or the polypeptide may be linked to a phosphatidylinositol lipid anchor through a carbohydrate bridge ("GPI-linked").

The term "deglycosylation" as used herein refers to methods for removing one or more covalently bound carbohydrate residues from polypeptides. While removal of all covalently bound carbohydrate residues is preferred, a polypeptide is considered to have been deglycosylated if any covalently bound carbohydrate residues have been removed. Enzymatic treatments, non-enzymatic treatments, or a combination of the two may be employed to remove covalently bound carbohydrate residues from polypeptides. It is preferred that at least about 50%, more preferably, at least about 60%, still more preferably at least about 70%, yet more preferably at least about 80%, and most preferably at least about 90% to about 100% of the carbohydrate residues are removed from a polypeptide.

As used herein, the term "purified" in reference to polypeptides does not require absolute purity. Instead, it represents an indication that the polypeptide(s) of interest is(are) in a discrete environment in which abundance (on a mass basis) relative to other proteins is greater than in a biological sample. By "discrete environment" is meant a single medium, such as a single solution, a single gel, a single precipitate, etc. Purified polypeptides may be obtained by a number of methods including, for example, laboratory synthesis, chromatography, preparative electrophoresis, centrifugation, precipitation, affinity purification, etc. One or more "purified" polypeptides of interest are preferably at least 10% of the protein content of the discrete environment. One or more "substantially purified" polypeptides are at least 50% of the protein content of the discrete environment, more preferably at least 75% of the protein content of the discrete environment, and most preferably at least 95% of the protein content of the discrete environment. Protein content is determined using a modification of the method of Lowry et al., *J. Biol. Chem.* 193: 265, 1951, described by Hartree, *Anal Biochem* 48: 422-427 (1972), using bovine serum albumin as a protein standard.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3rd Edition, W. E. Paul, ed., Raven Press, N.Y. (1993); Wilson (1994) *J. Immunol. Methods* 175: 267-273; Yarmush (1992) *J. Biochem. Biophys. Methods* 25: 85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341: 544-546), which consists of a VH domain; and (vi) an isolated complementarity determining region (CDR). Single chain antibodies, monoclonal antibodies, polyclonal antibodies, and antibodies obtained by molecular biological techniques (e.g., by phage display methods) are also included by reference in the term "antibody." Preferred antibodies are "Omniclonal" antibodies. By this is meant a mixture of different antibody molecules selected from a phage display library, where each antibody specifically binds to a target antigen with a minimum affinity of $10^9$ $M^{-1}$ to $10^{10}$ $M^{-1}$.

The term "specifically binds" is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ $M^{-1}$. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c = K(n-r)$:

where r=moles of bound ligand/mole of receptor at equilibrium;

c=free ligand concentration at equilibrium;

K=equilibrium association constant; and n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "discrete" as used herein refers to areas of a surface that are non-contiguous. That is, two areas are discrete from one another if a border that is not part of either area completely surrounds each of the two areas. The term "independently addressable" as used herein refers to discrete areas of a surface from which a specific signal may be obtained.

One skilled in the art will appreciate that antibody zones can also be independent of each other, but can be in contact with each other on a surface.

The term "test sample" as used herein refers to a sample in which the presence or amount of one or more analytes of interest are unknown and to be determined in an assay, preferably an immunoassay. Preferably, a test sample is a bodily fluid obtained for the purpose of diagnosis, prognosis, or evaluation of a subject, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components. Preferred samples may be obtained from bacteria, viruses and animals, such as dogs and cats. Particularly preferred samples are obtained from humans. By way of contrast, a "standard sample" refers to a sample in which the presence or amount of one or more analytes of interest are known prior to assay for the one or more analytes.

The term "disease sample" as used herein refers to a tissue sample obtained from a subject that has been determined to suffer from a given disease. Methods for clinical diagnosis are well known to those of skill in the art. See, e.g., *Kelley's Textbook of Internal Medicine*, 4$^{th}$ Ed., Lippincott Williams & Wilkins, Philadelphia, Pa., 2000; *The Merck Manual of Diagnosis and Therapy*, 17$^{th}$ Ed., Merck Research Laboratories, Whitehouse Station, N.J., 1999.

The term "subject-derived marker" as used herein refers to protein, polypeptide, phospholipid, nucleic acid, prion, glycoprotein, proteoglycan, glycolipid, lipid, lipoprotein, carbohydrate, or small molecule markers that are expressed or produced by one or more cells of the subject. The presence, absence, amount, or change in amount of one or more markers may indicate that a particular disease is present, or may indicate that a particular disease is absent.

The term "about" as used herein refers to +/−10% of a given number.

Use of Natriuretic Peptide Fragments as Prognostic and Diagnostic Markers

As noted above, increased blood levels of natriuretic peptides have been found in certain disease states, suggesting a role in the pathophysiology of those diseases, including stroke, congestive heart failure (CHF), cardiac ischemia, systemic hypertension, and acute myocardial infarction. See, e.g., WO 02/089657; WO 02/083913; WO 03/016910; Hunt et al., *Biochem. Biophys. Res. Comm.* 214: 1175-83 (1995); Venugopal, *J. Clin. Pharm. Ther.* 26: 15-31, 2001; and Kalra et al., *Circulation* 107: 571-3, 2003; each of which is hereby incorporated in its entirety, including all tables, figures, and claims. The natriuretic peptides, alone, collectively, and/or together with additional proteins, can also serve as disease markers and indicators of prognosis in various cardiovascular conditions.

As described in PCT/US04/26984, filed Apr. 15, 2004, the amino terminal regions of both proBNP and mature BNP are targets for prolyl-specific dipeptidyl peptidases, and the amino terminal residues of these peptides have been demonstrated to be susceptible to degradation. Likewise, the carboxyl terminal region of both proBNP and mature BNP are also subject to degradation. Failure to consider the various natriuretic peptide fragments that may be present in a clinical sample when measuring one or more of the natriuretic peptides may have serious consequences for the accuracy of any diagnostic or prognostic method. Consider for example a simple case, where a sandwich immunoassay is provided for pro-BNP, and a significant amount (e.g., 50%) of the pro-BNP that had been present has now been degraded, resulting in a loss of residues from the amino and/or carboxyl terminus. An immunoassay formulated with antibodies that bind a region remaining in the pro-BNP fragment(s) will overestimate the amount of full length pro-BNP present in the sample, potentially resulting in a "false positive" result in an assay if only full length pro-BNP is of interest.

Overestimation of the natriuretic peptide concentration of a sample may have serious consequences for patient management. For example, a pro-BNP concentration may be used to determine if therapy for congestive heart failure is effective (e.g., by monitoring pro-BNP to see if an elevated level is returing to normal upon treatment). The same "false positive" pro-BNP result discussed above may lead the physician to continue, increase, or modify treatment (e.g., increase the dosage of diuretic, ACE inhibitor, digoxin, β-blocker, calcium channel blocker, and/or vasodialtor, or even consider surgical intervention) because of the false impression that current therapy is ineffective.

Moreover, the failure to consider the various natriuretic peptide fragments that may be present in a clinical sample may explain the so-called "endocrine paradox" in heart failure. As described by Goetze in *Clin. Chem.* 50: 1503-1510, 2004, heart failure patients have highly increased plasma concentrations of BNP. Surprisingly, however, these patients do not exhibit increased natriuresis. In fact, the opposite is true, as heart failure patients suffer from congestion, sodium retention, and edema. A further surprise is that these same patients do respond to administration of exogenous BNP with the expected increase in natriuresis. While not intending to be limited to a particular explanation for the endocrine paradox, it is likely that the increased plasma concentrations of BNP observed in such patients are due, at least in part, to the inability of various BNP assays to distinguish BNP fragments from BNP having intact amino and/or carboxyl termini.

While the present invention describes in detail the use of assays directed to specific fragments (e.g., $BNP_{77-108}$, $BNP_{3-108}$, etc.) in the diagnosis and prognosis of one or more conditions falling within the term "acute coronary syndromes," this exemplary embodiment is not meant to be limiting. Measurement of pro-BNP and its fragments may be applied to the diagnosis and/or prognosis of cardiovascular conditions generally. The term "cardiovascular conditions" refers to a diverse set of disorders of the heart and vasculature, including atherosclerosis, ischemic stroke, intracerebral hemorrhage, subarachnoid hemorrhage, transient ischemic attack, systolic dysfunction, diastolic dysfunction, aneurysm, aortic dissection, myocardial ischemia, angina pectoris, myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and acute coronary syndromes.

The term "acute coronary syndromes" ("ACS") has been applied to a group of coronary disorders that result from ischemic insult to the heart. Patients with ACS form a heterogeneous group, with differences in pathophysiology, clinical presentation, and risk for adverse events. Such patients present to the physician with conditions that span a continuum that includes stable angina, unstable angina, non-ST-elevation non-Q wave myocardial infarction ("NST"-"MI"), ST-elevation non-Q wave MI, and transmural (Q-wave) MI. ACS is believed to result largely from thrombus deposition and growth within one or more coronary arteries, resulting in a partial or complete occlusion of the artery, and frequently involves rupture of the plaque, resulting in an ischemic injury. ACS may also be precipitated by a coronary vasospasm or increased myocardial demand. For review, see, e.g., Davies, *Clin. Cardiol.* 20 (Supp. I): 12-17 (1997).

ACS is a manifestation of vascular injury to the heart, also referred to as myocardial injury or myocardial damage that is commonly secondary to atherosclerosis or hypertension, and is the leading cause of death in the United States. ACS is commonly caused by occlusion associated with coronary artery disease cause by atherosclerotic plaque formation and progression to either further occlusion or fissure. ACS can be manifested as stable angina, unstable angina, or myocardial infarction.

The seriousness of ACS is underlined by the morbidity and mortality that follow the ischemic insult. For example, workers have estimated that within four to six weeks of presentation with ACS, the risk of death or a subsequent myocardial infarction (MI) is 8-14%, and the rate of death, MI, or refractory ischemia is 15-25% (Theroux and Fuster, *Circulation* 97: 1195-1206, 1998). Given that the total number of deaths in the U.S. from acute MI is about 600,000, the search within the art for information that relates to the diagnosis, prognosis, and management of ACS has understandably been extensive. Several potential markers that may provide such information in certain patient populations have been identified, including circulating cardiac troponin levels (see, e.g., Antman et al., *N. Eng. J. Med.* 335: 1342-9, 1996; see also U.S. Pat. Nos. 6,147,688, 6,156,521, 5,947,124, and 5,795,725, each of which is hereby incorporated by reference in its entirety), ST-segment depression (see, e.g., Savonitto et al., *JAMA* 281: 707-13, 1999), circulating creatine kinase levels (see, e.g., Alexander et al., *Circulation* (Suppl.) 1629, 1998), and circulating c-reactive protein levels (see, e.g., Morrow et al., *J. Am. Coll. Cardiol.* 31: 1460-5, 1998).

Stable angina is characterized by constricting chest pain that occurs upon exertion or stress, and is relieved by rest or sublingual nitroglycerin. Unstable angina is characterized by constricting chest pain at rest that is relieved by sublingual nitroglycerin. Anginal chest pain is usually relieved by sublingual nitroglycerin, and the pain usually subsides within 30 minutes. Myocardial infarction is characterized by constricting chest pain lasting longer than 30 minutes that can be accompanied by diagnostic electrocardiography (ECG) Q waves. Unstable angina is thought to represent the clinical state between stable angina and myocardial infarction, and is commonly associated with atherosclerotic plaque rupture and thrombus formation. In this regard, atherosclerotic plaque rupture is the most common cause of myocardial infarction.

Inflammation occurs during stable angina, and markers of plaque rupture, platelet activation, and early thrombosis can be used to identify and monitor the progressing severity of unstable angina. The myocardial damage caused during an anginal attack is, by definition, reversible, while damage caused during a myocardial infarction is irreversible. According to this model, a specific marker of myocardial injury can be used to identify myocardial infarction. The progression of coronary artery disease from mild unstable angina to severe unstable angina and myocardial infarction is related to plaque instability and the degree of arterial occlusion. This progression can occur slowly, as stable plaques enlarge and become more occlusive, or it can occur rapidly, as unstable plaques rupture, causing platelet activation and occlusive thrombus formation. Because myocardial infarction most frequently shares the same pathophysiology as unstable angina, it is possible that the only distinction between these two events is the reversibility of myocardial damage. However, since the only distinction between severe unstable angina and mild myocardial infarction is based on clinical judgement, markers of myocardial damage may also appear in the peripheral circulation of patients diagnosed as having unstable angina.

Current diagnostic methods for ACS commonly include clinical symptoms, electrocardiography (ECG), and the measurement of cardiac markers in the peripheral circulation. Angiography is also used in cases of severe chest pain usually associated with unstable angina and acute myocardial infarction (AMI). Patients with ACS frequently have constricting chest pain that often radiates to the neck, jaw, shoulders, or down the inside of the left or both arms and can have accompanying symptoms of dyspnea, diaphoresis, palpitations, light-headedness, and nausea. Myocardial ischemia can produce diagnostic ECG changes including Q waves and ST segment changes. Elevations of the plasma concentration of cardiac enzymes may reflect the degree of cardiac tissue necrosis associated with severe unstable angina and myocardial infarction.

It has been reported that removal of natriuretic peptides from the circulation involves degradation pathways. Indeed, inhibitors of neutral endopeptidase, which cleaves natriuretic peptides under certain circumstances, have been suggested to hold promise in treatment of certain cardiovascular diseases. See, e.g., Trindade and Rouleau, *Heart Fail. Monit.* 2: 2-7, 2001. It has also been reported that oxidation of methionine residues in the natriuretic peptides reduces the biological activity compared to reduced forms. Koyama et al., *Eur. J. Biochem.* 203: 425-32. For the purposes described herein, the methionine-oxidized forms may be considered products of degradation.

The term "diagnosis" as used herein refers to methods by which the skilled artisan can estimate and even determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future event in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of delayed adverse events in a patient, or the chance of future ACS.

The term "correlating," as used herein in reference to the use of diagnostic and prognostic indicators, refers to comparing the presence or amount of the indicator in a patient to its presence or amount in persons known to suffer from, or known to be at risk of, a given condition; or in persons known to be free of a given condition, i.e. "normal individuals". For example, a marker level in a patient sample can be compared to a level known to be associated with a specific type of ACS. The sample's marker level is said to have been correlated with a diagnosis; that is, the skilled artisan can use the marker level to determine whether the patient suffers from a specific type of ACS, and respond accordingly. Alternatively, the sample's marker level can be compared to a marker level known to be associated with a good outcome (e.g., the absence of ACS), such as an average level found in a population of normal individuals.

Measures of test accuracy may be obtained as described in Fischer et al., *Intensive Care Med.* 29: 1043-51, 2003, and used to determine the effectiveness of a given marker or panel of markers. These measures include sensitivity and specificity, predictive values, likelihood ratios, diagnostic odds ratios, and ROC curve areas. Suitable tests may exhibit one or more of the following results on these various measures:

at least 75% sensitivity, combined with at least 75% specificity;

ROC curve area of at least 0.7, more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20, and a negative likelihood ratio (calculated as (1-sensitivity)/specificity) of less than or equal to 0.3, more preferably less than or equal to 0.2, and most preferably less than or equal to 0.1.

Glycosylation of Natriuretic Peptides

Glycosylated polypeptides typically comprise N-linked sugars attached to the amino group of one or more asparagine residues; O-linked sugars attached to the hydroxyl group of one or more serine and/or threonine residues; or a combination of N- and O-linked sugars. Natriuretic peptides, including pro-BNP, may be glycosylated, and that glycosylation can significantly affect the ability of certain methods of detecting natriuretic peptides in samples.

Several approaches may be used to obviate the potential difficulties presented by glycosylation to a detection scheme. First, one may use chemical or enzymatic treatments to remove carbohydrate residues from the polypeptides, thereby shifting one or more of the naturietic peptides of interest to a "detectable" state if the presence of glycosylation disrupting accurate detection. Second, one may carefully select antibodies that bind to one or more regions of the naturietic peptides of interest that are not subject to interference by glycosylation to provide antibodies that are "insensitive" to a particular glycosylation state. Third, one may carefully select antibodies that bind to one or more regions of the naturietic peptides of interest that are glycosylated, but that exhibit reduced binding in the deglycosylated state, to provide antibodies that are "sensitive" to a particular glycosylation state. Fourth, one may carefully select antibodies that bind to one or more regions of the naturietic peptides of interest that are glycosylated, but that exhibit increased binding in the deglycosylated state, to provide antibodies that are "sensitive" to a particular glycosylation state. One may also combine these approaches as necessary or desired.

Effective enzymatic methods for removing N- and O-linked carbohydrate residues are well known in the art, using enzymes such as N-glycanase (also known as N-glycosidase), endoglycosidase H, endoglycosidase A, O-glycanase (also known as endo-α-N-acetylgalactosaminidase), α2-(3,6,8,9)-neuriminidase, β(1,4)-galactosidase, N-acetylglucosaminidase, endoglycosidase $F_1$, endoglycosidase $F_2$, and/or endoglycosidase $F_3$. This list is not meant to be limiting. Such enzymatic methods of sugar removal from peptides may be used on native (non-denatured) peptides. In such enzymatic methods, however, denaturation of the glycopeptide may be employed, often with an increased rate of deglycosylation. Common denaturation conditions comprise the addition of about 0.01% to about 1% sodium dodecyl sulfate ("SDS"), and optionally about 5 mM to about 500 mM β-mercaptoethanol, in a buffer solution at about neutral pH (i.e., between about pH 6.5 and about pH 8). Such methods may further comprise from about 0.2% to about 2% NP-40, which can serve to stabilize some deglycosylation enzymes. Increased temperature (e.g., about 37° C. for from about 0.5 hours to about 48 hours) may also be employed together with such denaturation conditions.

In the case of non-enzymatic chemical treatments for removal of covalently bound carbohydrate residues from peptides, hydrazine hydrolysis has been found to be effective in the release of unreduced O- and N-linked oligosaccharides. Selective and sequential release of oligosaccharides can be accomplished by initial mild hydrazinolysis of the O-linked oligosaccharides at about 60° C. followed by N-linked oligosaccharides at about 95° C. See, e.g., Patel and Rarekh, *Meth. Enzymol.* 230, 58-66, 1994. Such treatment may result in destruction of the polypeptide however. Alkaline-β-elimination of O-linked oligosaccharides, which utilizes alkaline sodium borohydride in a mild base environment, may be preferred. See, e.g., *Glycobiology: A Practical Approach*, Fukuda, M. and Kobata, A. (Eds), pp. 291-328, IRL/Oxford Univ. Press, Oxford, 1993. In addition, trifluoromethanesulfonic acid hydrolysis may be employed. This method typically leaves an intact polypeptide, but results in destruction of the glycan, as glycosyl linkages between sugars are sensitive to cleavage by trifluoromethanesulfonic acid, but peptide bonds are stable to even prolonged treatment. See, e.g., Edge, *Biochem. J.* 376: 339-50, 2003.

Importantly, changes in mass observed in peptides following such enzymatic or trifluoromethanesulfonic acid treatment can be ascribed to removal of sugar residues, as post-translational modifications other than glycosylation are believed to be stable to such treatments. This can allow for better understanding of the relative contribution of carbohydrates and glycosylation sites to the antigenic epitopes on the polypeptides of interest. Deglycoylation can also allow better understanding of differences in polypeptide mass (e.g., the mass of the natriuretic peptides of interest and fragments thereof present in a sample, which can be related by methods well known to those of skill in the art to the sequence), as the removal of sugar residues removes any doubt as to whether differences in mass observed may be due to differences in sugar content rather than amino acid content.

The foregoing methods of sugar removal from peptides may be used on native (non-denatured) polypeptides and/or following denaturation of the polypeptides. Whether enzymatic, non-enzymatic, or both treatments are employed to remove covalently bound carbohydrate residues from natriuretic peptides, it is preferred that at least about 50%, more preferably, at least about 60%, still more preferably at least about 70%, yet more preferably at least about 80%, and most preferably at least about 90% to about 100% of the carbohydrate residues are removed from one or more, and preferably all, of the glycosylated natriuretic peptides of interest by this treatment. The extent of glycosylation of a polypeptide can be determined by comparing the apparent mass of the polypeptide to the mass of the amino acid constituents of the polypeptide, and assuming that the balance of the apparent mass is contributed by glycosylation. In the event that other modifications (e.g., oxidation, nitration, phosphorylation) are known to have occurred, the mass contributed by these other modifications may also be subtracted from the apparent mass. The extent of carbohydrate residue removal can then be monitored by determining the apparent mass of the polypeptide following deglycosylation treatment. Methods for determining the apparent mass of a polypeptide (e.g., SDS gel electrophoresis, analytical centrifugation, gel permeation chromatography, mass spectrometry, etc.) are well known to those of skill in the art.

The sample containing such glycosylated natriuretic peptides may be a test sample as that term is defined herein. The glycosylated natriuretic peptides present in such a sample may be naturally present, such as in a sample obtained from a patient, or may be a standard sample. Natriuretic peptides used in formulating such standards are often expressed recombinantly in mammalian tissue culture systems, which contain active glycosylation functions.

Following the deglycosylation step, the artisan may employ any assay methods known in the art. Such assay methods may employ separation methods such as affinity separation, gel electrophoresis, capillary electrophoresis, liquid chromatography, and/or HPLC to separate analytes of interest for detection. In preferred embodiments, immunoassay devices and methods, in various sandwich, competitive, or non-competitive assay formats, are used to generate a signal that is related to the presence or amount of one or more natriuretic peptides of interest.

In addition, mass spectrometry methods may advantageously be employed as part of the assay method. The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces; " U.S. Pat. No. 6,107,623, entitled "Methods and Apparatus for Tandem Mass Spectrometry; " U.S. Pat. No. 6,268,144, entitled "DNA Diagnostics Based On Mass Spectrometry; " U.S. Pat. No. 6,124,137, entitled "Surface-Enhanced Photolabile Attachment And Release For Desorption And Detection Of Analytes; " Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Molecules (e.g., peptides) in a test sample can be ionized by any method known to the skilled artisan. These methods include, but are not limited to, electron ionization, chemical ionization, fast atom bombardment, field desorption, and matrix-assisted laser desorption ionization ("MALDI"), surface enhanced laser desorption ionization ("SELDI"), photon ionization, electrospray, and inductively coupled plasma.

In certain embodiments, the MS methods discussed above are preferably combined with an affinity purification step such as binding to an antibody that specifically binds one or more polypeptides of interest. See, e.g., Nelson et al., *Anal. Chem.*, 67: 1153, 1995; Tubbs et al., *Anal. Biochem.* 289: 26, 2001. Niederkofler et al., *Anal. Chem.* 73: 3294, 2001.

One feature of glycoproteins is the typical heterogeneity of the glycans. It is very common for individual molecules of a given glycoprotein to carry different carbohydrates at the same attachment site in the polypeptide chain. Any structural changes in the carbohydrate residues will result in the formation of discrete molecular subsets referred to as glycoforms. In the case of various separation methods, such heterogeneity can substantially complicate the analysis due to differences in charge and mass of the various polypeptides of interest and/or differences in the binding of the various polypeptides of interest to a binding matrix (e.g., an antibody). In addition, carbohydrates are not ionized as efficiently as compounds such as proteins that can be easily protonated; neither do they appear to be transferred to the vapor phase as effectively.

Thus, in preferred embodiments, the methods described herein provide an increased detection of one or more naturietic peptides of interest, as compared to performing the same assaying step in the absence of removing one or more covalently bound carbohydrate residues from one or more of the natriuretic peptides of interest. The term "increased detection" as used herein refers to an increased signal obtained from the assay method for one or more particular naturietic peptides of interest. Such an increased signal may be representative of an increased ability to detect all of the naturietic peptides of interest. For example, an antibody that could not bind certain glycosylated forms of one or more naturietic peptides of interest would result in an assay signal that underestimates the concentration of those naturietic peptides; or less efficient ionization of certain glycosylated forms of one or more naturietic peptides of interest would result in an assay signal by MS that underestimates the concentration of those naturietic peptides. Deglycosylation can result in an increased assay signal. Such an increased signal may also be representative of an increased ability to detect one or more specific forms of the naturietic peptides of interest. For example, the heterogeneity of the glycans may result in separation of a single polypeptide into a plurality of different fractions in a separation method (e.g., those based on mass and/or charge). Deglycosylation can result in coalescence of those different fractions into a single fraction, thus providing an improved assay signal for that fraction.

In various embodiments, the increased detection of one or more naturietic peptides of interest, as compared to performing the same assaying step in the absence of removing one or more covalently bound carbohydrate residues from one or more of the natriuretic peptides of interest, is measured by an assay signal that increases by at least about 5%, more preferably at least about 10%, still more preferably at least about 20%, even more preferably at least about 50%, still more preferably at least about 100%, and most preferably at least about 200% or more.

The term "removal of one or more covalently bound carbohydrate residues" in this context does not necessarily refer to the use of enzymatic or non-enzymatic chemical treatments to remove existing carbohydrate residues from a polypeptide. Instead, it is meant to encompass any method for generating a polypeptide lacking one or more covalently bound carbohydrate residues. For example, solid phase synthesis methods may be used to generate a polypeptide that is free of all carbohydrate residues for use in such antibody screening methods. It is preferred that at least about 50%, more preferably, at least about 60%, still more preferably at least about 70%, yet more preferably at least about 80%, and most preferably at least about 90% to about 100% of the carbohydrate residues are removed from one or more, and preferably all, of the glycosylated natriuretic peptides of interest for use in the screening methods described herein.

Selection of Antibodies

The generation and selection of antibodies that are sensitive or insensitive to the degradation state of pro-BNP and mature BNP may be accomplished several ways. For example, one way is to purify fragments or to synthesize the fragments of interest using, e.g., solid phase peptide synthesis methods well known in the art. See, e.g., *Guide to Protein*

Purification, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified natriuretic peptide(s) of interest (e.g., pro-BNP or one of its fragments) and, if required, comparing the results to the affinity and specificity of the antibodies with natriuretic peptide(s) that are desired to be excluded from binding. The screening procedure can involve immobilization of the purified natriuretic fragments in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized natriuretic peptide(s) and fragment(s) are present. A similar approach may be used to screen glycosylation-insensitive antibodies. In this case, screening may take place using purified natriuretic fragments containing and lacking one or more carbohydrate residues.

The antibodies so identified may then be further analyzed for affinity and specificity to the natriuretic peptide(s) of interest in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various natriuretic peptides, but these approaches do not change the scope of the invention.

Use of Natriuretic Peptides in Marker Panels

Methods and systems for the identification of one or more markers for the diagnosis, and in particular for the differential diagnosis, of disease have been described previously. Suitable methods for identifying markers useful for the diagnosis of disease states are described in detail in U.S. patent application Ser. No. 10/331,127, entitled METHOD AND SYSTEM FOR DISEASE DETECTION USING MARKER COMBINATIONS, filed Dec. 27, 2002, which is hereby incorporated by reference in its entirety, including all tables, figures, and claims. One skilled in the art will also recognize that univariate analysis of markers can be performed and the data from the univariate analyses of multiple markers can be combined to form panels of markers to differentiate different disease conditions.

In developing a panel of markers useful in diagnosis, data for a number of potential markers may be obtained from a group of subjects by testing for the presence or level of certain markers. The group of subjects is divided into two sets, and preferably the first set and the second set each have an approximately equal number of subjects. The first set includes subjects who have been confirmed as having a disease or, more generally, being in a first condition state. For example, this first set of patients may be those that have recently had a disease incidence, or may be those having a specific type of disease. The confirmation of the condition state may be made through a more rigorous and/or expensive testing such as MRI or CT. Hereinafter, subjects in this first set will be referred to as "diseased".

The second set of subjects is simply those who do not fall within the first set. Subjects in this second set may be "non-diseased;" that is, normal subjects. Alternatively, subjects in this second set may be selected to exhibit one symptom or a constellation of symptoms that mimic those symptoms exhibited by the "diseased" subjects. In still another alternative, this second set may represent those at a different time point from disease incidence.

The data obtained from subjects in these sets includes levels of a plurality of markers, including for purposes of the present invention, one or more fragments of natriuretic peptides either measured individually or as a group. Preferably, data for the same set of markers is available for each patient. This set of markers may include all candidate markers which may be suspected as being relevant to the detection of a particular disease or condition. Actual known relevance is not required. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

A marker often is incapable of definitively identifying a patient as either diseased or non-diseased. For example, if a patient is measured as having a marker level that falls within the overlapping region, the results of the test will be useless in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known to those skilled in the art.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. In a preferred embodiment, the panel response (R) for a each subject (j) is expressed as:

$$R_j = \Sigma w_i I_{i,j},$$

where i is the marker index, j is the subject index, $w_i$ is the weighting coefficient for marker i, I is the indicator value to which the marker level for marker i is mapped for subject j, and $\Sigma$ is the summation over all candidate markers i.

One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known to those skilled in the art and include several commonly available minimizing or maximizing functions including the Simplex method and other constrained optimization techniques. It is understood by those skilled in the art that some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

Use of Natriuretic Peptides for Determining a Treatment Regimen

A useful diagnostic or prognostic indicator such as the various natriuretic peptides described herein can help clinicians select between alternative therapeutic regimens. For example, patients with elevation in cardiac troponin T or I following an acute coronary syndrome appear to derive specific benefit from an early aggressive strategy that includes potent antiplatelet and antithrombotic therapy, and early revascularization. Hamm et al., *N. Engl. J. Med.* 340: 1623-9 (1999); Morrow et al., *J. Am. Coll. Cardiol.* 36: 1812-7 (2000); Cannon et al., *Am. J. Cardiol.* 82: 731-6 (1998). Additionally, patients with elevation in C-reactive protein following myocardial infarction appear to derive particular benefit from HMG-CoA Reductase Inhibitor therapy. Ridker et al., *Circulation* 98: 839-44 (1998). Among patients with congestive heart failure, pilot studies suggest that ACE inhibitors may reduce BNP levels in a dose dependent manner. Van Veldhuisen et al., *J. Am. Coll. Cardiol.* 32: 1811-8 (1998).

Similarly, "tailoring" diuretic and vasodilator therapy based on the level of one or more natriuretic peptides may improve outcomes. See, e.g., Troughton et al., *Lancet* 355: 1126-30 (2000). Finally, in a single pilot study of 16 patients found that randomization to an ACE inhibitor rather than placebo following Q-wave MI was associated with reduced BNP levels over the subsequent 6-month period. Motwani et al., *Lancet* 341: 1109-13 (1993). Because BNP is a counter-regulatory hormone with beneficial cardiac and renal effects, it is likely that a change in BNP concentration reflects improved ventricular function and reduced ventricular wall stress. A recent article demonstrates the correlation of NT pro-BNP and BNP assays (Fischer et al., *Clin. Chem.* 47: 591-594 (2001). It is a further objective of this invention that the concentration of natriuretic peptides, either individually or considered in groups of markers, can be used to guide diuretic and vasodilator therapy to improve patient outcome. Additionally, the measurement of natriuretic peptides, either individually or considered in groups of markers, for use as a prognostic indicator for patients is within the scope of the present invention.

Recent studies in patients hospitalized with congestive heart failure suggest that serial BNP measurements may provide incremental prognositic information as compared to a single measurement; that is, assays can demonstrate an improving prognosis when BNP falls after therapy than when it remains persistently elevated. Cheng et al., *J. Am. Coll. Cardiol.* 37: 386-91 (2001). Thus, serial measurements of natriuretic peptides according to the present invention may increase the prognostic and/or diagnostic value of a marker in patients, and is thus within the scope of the present invention.

Assay Measurement Srategies

Numerous methods and devices are well known to the skilled artisan for the detection and analysis of polypeptides or proteins in test samples. In preferred embodiments, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman Access, Abbott AxSym, Roche ElecSys, Dade Behring Stratus systems are among the immunoassay analyzers that are capable of performing the immunoassays taught herein. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the one or more polypeptides is also contemplated by the present invention. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of polypeptides may be carried out separately or simultaneously with one test sample. For separate or sequential assay, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of polypeptides on a single surface. Particularly useful physical formats comprise surfaces having a plurality of discrete, adressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., one or more polypeptides of the invention) for detection at each location. Surfaces may alternatively comprise one or more discrete particles (e.g., microparticles or nanoparticles) immobilized at discrete locations of a surface, where the microparticles comprise antibodies to immobilize one analyte (e.g., one or more polypeptides of the invention) for detection.

In addition, one skilled in the art would recognize the value of testing multiple samples (for example, at successive time points) from the same individual. Such testing of serial samples will allow the identification of changes in polypeptide levels over time. Increases or decreases in polypeptide levels, as well as the absence of change in such levels, would provide useful information about the disease status that includes, but is not limited to identifying the approximate time from onset of the event, the presence and amount of salvagable tissue, the appropriateness of drug therapies, the effectiveness of various therapies as indicated by reperfusion or resolution of symptoms, differentiation of the various types of disease having similar symptoms, identification of the severity of the event, identification of the disease severity, and identification of the patient's outcome, including risk of future events.

A panel consisting of the polypeptides referenced above, and optionally including other protein markers useful in diagnosis, prognosis, or differentiation of disease, may be constructed to provide relevant information related to differential diagnosis. Such a panel may be constructed to detect 1, 2, 3, 4, 5, 6, 7, 8, 9, 10, 15, 20, or more or individual analytes, including one or more polypeptides of the present invention. The analysis of a single analyte or subsets of analytes could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single analyte or a subset of analytes in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W. B. Saunders and Company, p. 496).

The analysis of analytes could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In certain embodiments, the signal obtained from an assay need not be related to the presence or amount of one or more natriuretic peptide(s); rather, the signal may be directly related to the presence or absence of a disease, or the likelihood of a future adverse outcome related to a disease. For example, a level of signal x may indicate that y pg/mL of a natriuretic peptide is present in the sample. A table may then indicate that y pg/mL of that natriuretic peptide indicates congestive heart failure. It may be equally valid to simply relate a level of signal x directly to congestive heart failure, without determining how much of the natriuretic peptide is present. Such a signal is preferably obtained from an immunoassay using the antibodies of the present invention, although other methods are well known to those skilled in the art.

As discussed above, samples may continue to degrade the natriuretic peptides or fragments thereof, even once the sample is obtained. Thus, it may be advantageous to add one or more protease inhibitors to samples prior to assay. Numerous protease inhibitors are known to those of skill in the art, and exemplary inhibitors may be found in, e.g., The Complete Guide for Protease Inhibition, Roche Molecular Biochemicals, updated Jun. 3, 1999 at http://www.roche-applied-science.com/fst/products.htm?/prod_inf/manuals/protease/prot_toc.htm, and European Patent Application 03013792.1 (published as EP 1 378 242 A1), each of which is hereby incorporated in its entirety. Because various metalloproteases and calcium-dependent proteases are known to exist in blood-derived samples, chelators such as EGTA and/or EDTA, also act as protease inhibitors. In addition, or in the alternative, inhibitors of neutral endopeptidase and/or dipeptidyl peptidase may be used.

EXAMPLES

The following examples serve to illustrate the present invention. These examples are in no way intended to limit the scope of the invention.

Example 1

Blood Sampling

Blood is preferably collected by venous puncture using a 20 gauge multi-sample needle and evacuated tubes, although fingertip puncture, plantar surface puncture, earlobe puncture, etc., may suffice for small volumes. For whole blood collection, blood specimens are collected by trained study personnel in EDTA-containing blood collection tubes. For serum collection, blood specimens are collected by trained study personnel in thrombin-containing blood collection tubes. Blood is allowed to clot for 5-10 minutes, and serum is separated from insoluble material by centrifugation. For plasma collection, blood specimens are collected by trained study personnel in citrate-containing blood collection tubes and centrifuged for $\geq$12 minutes. Samples may be kept at 4° C. until use, or frozen at −20° C. or colder for longer term storage. Whole blood is preferably not frozen.

Example 2

Expression of $BNP_{3-108}$

PCR primers were made corresponding to sequence at the 5'-end of human $BNP_{3-108}$ and the coding sequence at the 3'-end of human pro-BNP (Genbank accession number M31776). The 5' PCR primers, in addition to a translation initiation site, introduce the codons for a murine kappa chain signal sequence immediately upstream and in frame with the third amino acid of human proBNP. The outer 5' primer contained 21 base pairs of vector sequence at its 5'-end corresponding to an EcoRI site and sequence immediately upstream. The 3' PCR primers introduced the codons for tags to assist in purification of the recombinant protein inserted between the end of the coding sequence and the stop codon by: a FLAG peptide tag, and a second tag suitable for metal-chelate affinity chromatography. The outer 3' primer also contained approximately 20 nucleotides of vector sequence, including 6 bases of a NotI site and the sequence immediately downstream, at its 5' end. The vector sequence at the 5'-ends of these primers formed, upon treatment with T4 DNA polymerase, single-stranded overhangs that were specific and complementary to those on the vector.

The primary PCR amplification of the $BNP_{3-108}$ gene insert was performed in a 50 μl reaction containing 50 pmol of 5' primer, 50 pmol of 3' primer, 1.25 units of Expand polymerase (Roche Diagnostics, Indianapolis, Ind.), 5 μl 2 mM dNTPs, 5 μl 10× Expand reaction buffer, 1 μl of Clontech Quick-clone human spleen cDNA (Clontech Laboratories, Palo Alto, Calif.) as template, and water to 50 μl. The reactions were carried out in a Perkin-Elmer thermal cycler as described in Example 18 of U.S. Pat. No. 6,057,098. The resulting PCR product was used as template for a secondary PCR amplification to add flanking vector sequence for cloning. The PCR amplification was performed in a 100 μl reaction (×2) each containing 100 pmol of 5' primer, 100 pmol of 3' primer, 2.5 units of Expand polymerase, 10 μl 2 mM dNTPs, 10 μl 10× Expand reaction buffer, 1 μl of the primary PCR reaction as template, and water to 100 μl. The PCR-products were precipitated and fractionated by agarose gel electrophoresis and full-length products excised from the gel, purified, and resuspended in water as described in Example 17 of U.S. Pat. No. 6,057,098.

The cloning vector was prepared to receive insert by digestion with NotI and EcoRI The insert and EcoRI/NotI digested vector (1.0 μg of DNA) was digested for 4 minutes at 30° C. with 1 μl (1 U/μl) of T4 DNA polymerase. The T4 DNA polymerase was heat inactivated by incubation at 70° C. for 10 minutes. The samples were cooled, briefly centrifuged, and 45 ng of the digested insert added to 100 ng of digested vector in a fresh microfuge tube. After the addition of 1.0 μl of 10× annealing buffer, the volume was brought to 10 μl with water. The mixture was heated to 70° C. for 2 minutes and cooled over 20 minutes to room temperature, allowing the insert and vector to anneal. The annealed DNA was diluted one to four with distilled water and electroporated as described in Example 8 of U.S. Pat. No. 6,057,098 into 30 μl of electrocompetent E. coli strain, DH10B (Invitrogen, Carlsbad, Calif.).

The transformed cells were diluted to 1.0 ml with 2×YT broth and 10 μl, 100 μl, 300 μl plated on LB agar plates supplemented with ampicillin (75 μg/ml) and grown overnight at 37° C. Colonies were picked and grown overnight in 2×YT (75 μg/ml ampicillin at 37° C. The following day glycerol stocks were made for long-term storage at −80° C. The sequence of the $BNP_{3-108}$ clones was verified by sequencing. Plasmid suitable for transfection and the subsequent expression and purification of human $BNP_{3-108}$ was prepared (clone proBNP4.2) using an EndoFree Plasmid Mega Kit as per manufacturers' recommendations (Qiagen, Valencia, Calif.).

Cells were transfected with proBNP4.2 plasmid, the cell broths from several transfections were pooled, an EDTA-free proteinase inhibitor cocktail was added (Roche Applied Science, Indianapolis, Ind.), spun down at 3500 rpm for 20 min, and the supernatant was saved for purification of $BNP_{3-108}$. The supernatant (1.6 L) was adjusted to 15 mM imidazole and 6 ml of Chelating Fast Flow resin (Amersham Pharmacia Biotech, Piscataway, N.J.) charged with $NiCl_2$, was added and allowed to incubate for 2.5 hours. The supernatant was passed through a column to capture and pack the resin. The column was washed with BBS (20 mM borate, 150 mM NaCl, 0.01% $NaN_3$), 10 mM imidazole, and eluted with BBS, 200 mM imidazole. The eluate was brought up to 25 ml with BBS and loaded onto a column with 5 ml anti-FLAG immunoaffinity resin (Sigma, St. Louis, Mo.), pre-equilibrated with a BBS. The column was washed with BBS, and the $BNP_{3-108}$ was eluted with 4 mls 0.1M glycine buffer, pH 3.0. The eluate was supplemented with NaCl to 150 mM, the pH adjusted to 8.0 with 2M TRIS and the sample dialyzed into BBS, pH 8.0. The purified protein was approximately 0.2 mg/ml, and aliquots were stored at −80° C. BNP$_{3-108}$ was biotinylated as described in Example 9 of U.S. Pat. No. 6,057,098.

Example 3

Recombinant Antibody Preparation

Immunization of Mice with Antigens and Purification of RNA From Mouse Spleens

Two species of mice were used for immunization: Balb/c (Charles River Laboratories, Wilmington, Mass.) and A/J (Jackson Laboratories, Bar Harbor, Me.). Each of ten mice were immunized intraperitoneally with antigen using 50 μg protein in adjuvant (e.g., Freund's complete or Quil A) on day 0, 14, and 28. Tests bleeds of mice were obtained through puncture of the retro-orbital sinus. The mice were boosted with 50 μg of protein on days 42 and 43.

On day 45, the spleens were harvested, macerated, and the spleen suspension pulled through an 18 gauge needle until viscous and all cells are lysed, then transferred to a microcentrifuge tube. The sample was divided evenly between two microcentrifuge tubes and the following added in order, with mixing by inversion after each addition: 100 μl 2 M sodium acetate (pH 4.0), 1.0 ml water-saturated phenol (Fisher Scientific, Pittsburgh, Pa.), 200 μl chloroform/isoamyl alcohol 49:1 (Fisher Scientific, Pittsburgh, Pa.). The solution was vortexed for 10 seconds and incubated on ice for 15 min. Following centrifugation at 14,000 rpm for 20 min at 2-8° C., the aqueous phase was transferred to a fresh tube. An equal volume of water saturated phenol/chloroform/isoamyl alcohol (50:49:1) was added, and the tube vortexed for ten seconds. After a 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14,000 rpm for 20 min at 4° C., the supernatant was aspirated away, the tubes briefly spun and all traces of liquid removed.

The resulting RNA pellets were each dissolved in 300 μl of solution D, combined, and precipitated with an equal volume of isopropanol at −20° C. for a minimum of 30 min. The sample was centrifuged 14,000 rpm for 20 min at 4° C., the supernatant aspirated as before, and the sample rinsed with 100 μl of ice-cold 70% ethanol. The sample was again centrifuged 14,000 rpm for 20 min at 4° C., the 70% ethanol solution aspirated, and the RNA pellet dried in vacuo. The pellet was resuspended in 100 μl of sterile distilled water, and the RNA stored at −80° C.

Preparation of Complementary DNA (cDNA)

The total RNA purified as described above was used directly as template for preparation of cDNA. RNA (50 μg) was diluted to 100 μL with sterile water, and 10 μL-130 ng/mL oligo dT$_{12}$ is added. The sample was heated for 10 min at 70° C., then cooled on ice. 40 μL 5× first strand buffer was added (Gibco/BRL, Gaithersburg, Md.), 20 μL 0.1 M dithiothreitol (Gibco/BRL, Gaithersburg, Md.), 10 μL 20 mM deoxynucleoside triphosphates (dNTP's, Boehringer Mannheim, Indianapolis, Ind.), and 10 μL water on ice. The was then incubated at 37° C. for 2 min. 10 μL reverse transcriptase (Superscript II, Gibco/BRL, Gaithersburg, Md.) was added and incubation continued at 37° C. for 1 hr. The cDNA products are used directly for polymerase chain reaction (PCR).

Amplification of cDNA by PCR

To amplify substantially all of the H and L chain genes using PCR, primers were chosen that corresponded to substantially all published sequences. 33 oligonucleotides are synthesized to serve as 5' primers for the H chains, and 29 oligonucleotides are synthesized to serve as 5' primers for the kappa L chains, substantially as described in U.S. 20030104477. Amplification by PCR was performed separately for each pair of 5' and 3' primers. A 50 μL reaction was performed for each primer pair with 50 pmol of 5' primer, 50 pmol of 3' primer, 0.25 μL Taq DNA Polymerase (5 units/mL, Boehringer Mannheim, Indianapolis, Ind.), 3 μL cDNA (described in Example 2), 5 μL 2 mM dNTP's, 5 μL 10× Taq DNA polymerase buffer with MgC12 (Boehringer Mannheim, Indianapolis, Ind.), and H$_2$O to 50 μL. The dsDNA products of the PCR process were then subjected to asymmetric PCR using only 3' primer to generate substantially only the anti-sense strand of the target genes.

Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14,000 rpm for 10 min at 2-8° C. The supernatant was carefully aspirated, and the tubes briefly spun a 2nd time. The last drop of supernatant was removed with a pipet. The DNA was dried in vacuo for 10 min on medium heat. The H chain and L chain products were pooled separately in 210 μL water. The ss-DNA was purified by high performance liquid chromatography (HPLC), and the ss-DNA eluted from the HPLC collected in 0.5 min fractions. Fractions containing ss-DNA were ethanol precipitated, pelleted and dried as described above. The dried DNA pellets were pooled in 200 μL sterile water.

If desired, the ss-DNA was kinase-treated on the 5' end in preparation for mutagenesis. 24 μL 10× kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio)-chloroform-isoamy-1 alcohol (50:49:1) and one extraction with chloroform:isoamyl alcohol (49:1). After the extractions, the DNA was ethanol precipitated and pelleted as described above.

Antibody Phage Display Vector

The antibody phage display vector contained the DNA sequences encoding the heavy and light chains of a mouse monoclonal Fab fragment inserted into a vector substantially as described by Huse, WO 92/06024. To make the first derivative cloning vector, deletions were made in the variable regions of the H chain and the L chain by Kunkel, et al., Methods. Enzymol. 154: 367 (1987)). These mutations delete the region of each chain from the 5' end of CDR 1 to the 3' end of CDR3, and add a DNA sequence where protein translation would stop. The resulting cloning vector is called BS11.

Changes were made to BS11 to generate the cloning vector used in the present screening methods. The amber stop codon between the heavy chain and the pseudo gene VIII sequence was removed so that every heavy chain is expressed as a fusion protein with the gene VIII protein. A HindIII restriction enzyme site in the sequence between the 3' end of the L chain and the 5' end of the alkaline phosphatase signal sequence was deleted. The interchain cysteine residues at the carboxyl-terminus of the L and H chains were changed to serine residues. Nonessential DNA sequences on the 5' side of the lac promoter and on the 3' side of the pseudo gene VIII sequence were deleted. A transcriptional stop DNA sequence was added to the vector at the L chain cloning site. Finally, DNA sequences for protein tags were added to different vectors to allow enrichment for polyvalent phage by metal chelate chromatography or by affinity purification using a decapeptide tag and a magnetic latex having an immobilized antibody that binds the decapeptide tag.

Transformation of E. coli by Electroporation

Electrocompetent E. coli cells were thawed on ice. DNA was mixed with 20-40 μL electrocompetent cells by gently pipetting the cells up and down 2-3 times, being careful not to introduce air-bubbles. The cells were transferred to a Gene Pulser cuvette (0.2 cm gap, BioRAD, Hercules, Calif.) that has been cooled on ice, again being careful not to introduce an air-bubble in the transfer. The cuvette was placed in the E. coli Pulser (BioRAD, Hercules, Calif.) and electroporated with the voltage set at 1.88 kV according to the manufacturer's recommendation. The transformed sample was immediately diluted to 1 ml with 2× YT broth.

Example 4

Preparation of Biotinylated Antigens and Antibodies

Protein antigens or antibodies were dialyzed against a minimum of 100 volumes of 20 mM borate, 150 mM NaCl, pH 8 (BBS) at 2-8° C. for at least 4 hr. The buffer was changed at least once prior to biotinylation. Protein antigens or antibodies were reacted with biotin-XX-NHS ester (Molecular Probes, Eugene, Oreg., stock solution at 40 mM in dimethylformamide) at a final concentration of 1 mM for 1 hr at room temperature. After 1 hr, the protein antigens or antibodies were extensively dialyzed into BBS to remove unreacted small molecules.

Example 5

Preparation of Alkaline Phosphatase-Antigen Conjugates

Alkaline phosphatase (AP, Calzyme Laboratories, San Luis Obispo, Calif.) was placed into dialysis versus a minimum of 100 volumes of column buffer (50 mM potassium phosphate, 10 mM borate, 150 mM NaCl, 1 mM $MgSO_4$, pH 7.0) at 2-8° C. for at least four hr. The buffer was changed at least twice prior to use of the AP. The AP was diluted to 5 mg/mL with column buffer. The reaction of AP and succinimidyl 4-(N-maleimidomethyl) cyclohexane-1-carboxylate (SMCC, Pierce Chemical Co., Rockford, Ill.) was carried out using a 20:1 ratio of SMCC:AP. SMCC was dissolved in acetonitrile at 20 mg/mL and diluted by a factor of 84 when added to AP while vortexing or rapidly stirring. The solution was allowed to stand at room temperature for 90 min before the unreacted SMCC and low molecular weight reaction products were separated from the AP using gel filtration chromatography (G50 Fine, Pharmacia Biotech, Piscataway, N.J.) in a column equilibrated with column buffer.

Protein antigen was dialyzed versus a minimum of 100 volumes of 20 mM potassium phosphate, 4 mM borate, 150 mM NaCl, pH 7.0 at 2-8° C. for at least four hr. The buffer was changed at least twice prior to use of the antigen. The reaction of antigen and N-succinimidyl 3-[2-pyridyldithio]propionate (SPDP, Pierce Chemical Co., Rockford, Ill.) was carried out using a 20:1 molar ratio of SPDP:antigen. SPDP was dissolved in dimethylformamide at 40 mM and diluted into the antigen solution while vortexing. The solution was allowed to stand at room temperature for 90 min, at which time the reaction was quenched by adding taurine (Aldrich Chemical Co., Milwaukee, Wis.) to a final concentration of 20 mM for 5 min. Dithiothreitol (Fisher Scientific, Pittsburgh, Pa.) was added to the protein at a final concentration of 1 mM for 30 min. The low molecular weight reaction products were separated from the antigen using gel filtration chromatography in a column equilibrated in 50 mM potassium phosphate, 10 mM borate, 150 mM NaCl, 0.1 mM ethylene diamine tetraacetic acid (EDTA, Fisher Scientific, Pittsburgh, Pa.), pH 7.0.

The AP and antigen were mixed together in an equimolar ratio. The reaction was allowed to proceed at room temperature for 2 hr. The conjugate was diluted to 0.1 mg/mL with block containing 1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0.

Example 6

Preparation of Peptide Conjugates with Keyhole Limpet Hemocyanin and Bovine Serum Albumin.

Keyhole Limpet Hemocyanin (KLH) conjugates were made essentially as described in Example 21 of U.S. Pat. No. 6,057,098 with the following modifications: KLH-SMCC was reacted with a 2-fold excess of peptide thiol consisting of 90% specific cysteine containing peptide and 5% each of PADRE peptide having a cysteine at the N-terminus of the peptide and the C-terminus of the peptide (peptide 1024.03 from Alexander et al., *Immunity* 1: 751-761, 1994).

Bovine Serum Albumin (BSA) conjugates with peptide were made essentially as described in Example 21 of U.S. Pat. No. 6,057,098. The BSA biotin peptide conjugates were made by first biotinylating the BSA (Example 9 of U.S. Pat. No. 6,057,098), then conjugating with peptide.

Example 7

Preparation of Avidin Magnetic Latex

Magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

Example 8

Enrichment of Polyclonal Phage

The following peptides were synthesized to include a carboxyl terminal cysteine to provide a thiol for use in conjugation: $BNP_{1-8}$ (HPLGSPGSC) (SEQ ID NO: 2); $BNP_{1-12}$ (HPLGSPGSASDLC) (SEQ ID NO: 3); $BNP_{3-10}$ (LGSPGSASC) (SEQ ID NO: 4); and $BNP_{3-14}$ (LGSPGSASDLETC) (SEQ ID NO: 5).

Enrichment of Polyclonal Phage Specific to $BNP_{3-108}$

The first round antibody phage were generally prepared essentially as described in Example 7 of U.S. Pat. No. 6,057,098 from RNA isolated from mice immunized with $BNP_{3-10}$ conjugated to KLH and PADRE (pan-DR T-helper epitope). The antibody phage samples were panned with avidin magnetic latex generally as described in Example 16 of U.S. Pat. No. 6,057,098. The first round antibody phage samples (10 samples from 5 different spleens) were selected with $BNP_{3-14}$ conjugated via an SMCC linker to BSA-biotin ($5 \times 10^{-9}$ M final BSA concentration), with $10^{-6}$ M BSA-SMCC added to remove antibodies specific to the SMCC arm. The eluted phage were enriched with 7F11 magnetic latex, then the phage was panned a second time with $BNP_{3-14}$ conjugated to BSA-biotin at $5 \times 10^{-9}$ M final BSA concentration and $10^{-6}$ M BSA-SMCC. The phage eluted from the $2^{nd}$ round of panning were pooled, and the third round of panning was done with $BNP_{3-14}$ conjugated to BSA-biotin at $1 \times 10^{-9}$ M final BSA concentration, with unlabeled $BNP_{1-12}$ conjugated to BSA ($2 \times 10^{-7}$ M BSA) added to remove antibodies not specific to the N-terminus of the 3-10 peptide. The fourth and final round of selection was done with $BNP_{3-108}$ biotin at $1 \times 10^{-8}$ M final concentration. The selected phage were subcloned into a plasmid expression vector generally as described in Example 18 of U.S. Pat. No. 6,057,098.

Enrichment of Polyclonal Phage specific to $BNP_{1-108}$.

The first round antibody phage were generally prepared as described in Example 7 of U.S. Pat. No. 6,057,098 from RNA isolated from mice immunized with $BNP_{1-12}$ conjugated to KLH and PADRE. The antibody phage samples were panned with avidin magnetic latex generally as described in Example 16 of U.S. Pat. No. 6,057,098. The first round antibody phage samples (10 samples from 5 different spleens) were selected with $BNP_{1-8}$ conjugated to BSA-biotin ($5 \times 10^{-9}$ M final BSA concentration), with $10^{-6}$ M final concentration BSA-SMCC added to remove antibodies specific to the SMCC arm. The eluted phage were enriched with 7F11 magnetic latex, then the phage samples were panned a second time with $BNP_{1-8}$ conjugated to BSA-biotin ($5 \times 10^{-9}$ M final BSA concentration), with $10^{-6}$ M final concentration BSA-SMCC added. The phage samples eluted from the second round of panning were pooled, and the third round of panning was done as described above with the pooled phage. The fourth round of selection was done with $BNP_{1-8}$ conjugated to BSA-biotin($1 \times 10^{-9}$ M final BSA concentration) in the presence of unlabeled $BNP_{3-14}$ conjugated to BSA ($2 \times 10^{-7}$ M final BSA concentration) to remove antibodies not specific to the N-terminus of the 1-12 peptide. The fifth round of selection was done with $BNP_{1-108}$ conjugated to biotin at $1 \times 10^{-8}$ M final concentration. The sixth and final round of selection was done with $BNP_{1-108}$ conjugated to biotin at $1 \times 10^{-9}$ M final concentration and unlabeled $BNP_{3-108}$ at $5 \times 10^{-7}$ M final concentration. The selected phage sample were subcloned into a plasmid expression vector generally as described in Example 18 of U.S. Pat. No. 6,057,098.

Example 9

Biochemical Analyses

BNP species of interest are measured using standard immunoassay techniques. These techniques involve the use of antibodies to specifically bind the protein targets. An antibody directed against one or more forms of BNP (e.g., a $BNP_{1-108}$-specific or $BNP_{3-108}$-specific antibody) is biotinylated using N-hydroxysuccinimide biotin (NHS-biotin) at a ratio of about 5 NHS-biotin moieties per antibody. The biotinylated antibody is then added to wells of a standard avidin 384 well microtiter plate, and biotinylated antibody not bound to the plate is removed. This formes an anti-BNP solid phase in the microtiter plate. Another anti-BNP antibody (e.g., directed to a portion of $BNP_{77-108}$) is conjugated to alkaline phosphatase using standard techniques, using SMCC and SPDP (Pierce, Rockford, Ill.). The immunoassays are performed on a TECAN Genesis RSP 200/8 Workstation. Test samples (10 µL) are pipeted into the microtiter plate wells, and incubated for 60 min. The sample is then removed and the wells washed with a wash buffer, consisting of 20 mM borate (pH 7.42) containing 150 mM NaCl, 0.1% sodium azide, and 0.02% Tween-20. The alkaline phosphatase-antibody conjugate is then added to the wells and incubated for an additional 60 min, after which time, the antibody conjugate is removed and the wells washed with a wash buffer. A substrate, (AttoPhos®, Promega, Madison, Wis.) is added to the wells, and the rate of formation of the fluorescent product is related to the concentration of the BNP in the test samples.

Using a $BNP_{3-108}$-specific antibody paired to an antibody that binds $BNP_{77-108}$, a sandwich immunoassay was formulated that was specific to pro-BNP fragments in which the first two residues had been lost (designated "$BNP_{3-xx}$ fragments"). The minimum detectable level ("mdl") was calculated to be 150 pg/mL, using $BNP_{3-108}$ as a standard. Pro-BNP fragment levels measured in samples obtained from congestive heart failure patients and normal individuals were as follows:

| CHF patient ID | $BNP_{3-xx}$ fragment concentration (pg/mL) | Normal ID | $BNP_{3-xx}$ fragment concentration (pg/mL) |
| --- | --- | --- | --- |
| 1 | 10998 | 1 | <150 |
| 2 | 15018 | 2 | ≦mdl |
| 3 | 2008 | 3 | ≦mdl |
| 4 | 1928 | 4 | ≦mdl |
| 5 | 264 | 5 | ≦mdl |
| 6 | 2201 | 6 | ≦mdl |
| 7 | 2382 | 7 | ≦mdl |
| 8 | 6953 | 8 | ≦mdl |
| 9 | 8630 | 9 | ≦mdl |
| | | 10 | 191 |
| | | 11 | 252 |
| | | 12 | ≦mdl |
| | | 13 | ≦mdl |
| | | 14 | 276 |
| | | 15 | ≦mdl |
| | | 16 | ≦mdl |
| | | 17 | ≦mdl |
| | | 18 | ≦mdl |
| | | 19 | ≦mdl |
| | | 20 | ≦mdl |

Example 10

Analysis of Natriuretic Peptides by Mass Spectrometry

Preparation of Antibody Capture Surface

3 µL of antibody solution (0.25 mg/mL anti-BNP monoclonal antibody in borate buffered saline pH 8.0 ("BBS")) is applied to appropriate spots of a PS10 ProteinChip array (Ciphergen cat. # C553-0044), and the chip is placed in a humid chamber with gentle agitation at 20° C. for 3 hours. The antibody solution is removed, and the array spots are washed twice with 3 µL of 1.5 mg/mL BSA/0.1% Triton X-100/0.5 M Tris-HCl pH 8.0. At the second wash, the chip is placed in a humid chamber without agitation at 20° C. for 3 hours. Following this wash, the array is immersed in 5 mM HEPES pH 7.5, and the excess buffer is removed.

Capture of BNP

Using a BIOMEC robotic pipetting station (Beckman Instruments), the array is washed with 150 µL 1% Triton X-100 in BBS for 10 minutes; 150 µL 10% PEG300/0.1% Triton X-100 in BBS for 10 minutes; and 3× with 150 µL 0.2% Triton X-100 in BBS for 5 minutes each. 40 µL 0.2% Triton X-100 in BBS and 40 µL deglycosylated sample (or control sample) is applied and incubated overnight at 4° C. with gentle agitation.

Application of Energy Absorbing Matrix and MS Analysis

Following this incubation, the array is washed 3× with 150 µL 1M urea/0.1% CHAPS/0.3M KCl/50 mM Tris-HCl pH 7.5 for 1 minute each; and 3× with 300 µL 5 mM HEPES pH 7.5 for 3 seconds each. Excess buffer is removed, and the array is allowed to air dry until no sheen is visible. For low molecular weight analysis (M/Z≦6000), 1 µL of 20% α-cyano-4-hydroxycinnamic acid (CHCA, Ciphergen cat. # C300-0001) in 0.5% trifluoroacetic acid (Pierce cat # 28904)/50% acetonitrile (Pierce cat. # 20062) is applied to appropriate spots as an energy absorbing matrix ("EAM"). For high molecular weight analysis (MIZ≦6000), 1 µL of 50% sinapinic acid (SPA, Ciphergen Cat. No. C300-0002) in 0.5% trifluoroacetic acid/50% acetonitrile is applied to appropriate spots as an EAM. Spots are allowed to air dry, and a second 1 µL drop of the appropriate EAM is applied.

MS spectra are acquired using a Ciphergen ProteinChip reader model PBS IIC. For low molecular weight analysis, the following instrument parameters are used: high mass is set to 70 kDa optimized from 2 kDa to 15 kDa; starting laser intensity is set to 165; starting detector sensitivity is set to 9; mass deflector is set to 1 kDa; acquisition method is set to SELDI quantitation; SELDI acquisition parameters=26, delta=10, transients per=18, ending position=76; and warming positions with 5 shots at intensity=175. For high molecular weight analysis, the following instrument parameters are used: high mass is set to 70 kDa optimized from 3 kDa to 30 kDa; starting laser intensity is set to 200; starting detector sensitivity is set to 9; mass deflector is set to 2 kDa; acquisition method is set to SELDI quantitation; SELDI acquisition parameters=24, delta=10, transients per=13, ending position=74; and warming positions with 3 shots at intensity=210.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

I claim:

1. A method for detecting the presence or amount of one or more BNP related species of interest or one or more pro-BNP related species of interest in a sample obtained from a subject, comprising:
   (a) assaying said sample to provide an assay result related to the presence or amount of said BNP related species of interest in said sample, wherein said assay is sensitive to degradation of the amino terminus of BNP; or
   (b) assaying said sample to provide an assay result related to the presence or amount of said pro-BNP related species of interest in said sample, wherein said assay is sensitive to degradation of the amino terminus of pro-BNP; or
   performing both steps (a) and (b) wherein said assay in step (a), if performed, is configured such that BNP is detected with at least a 5-fold reduction in signal relative to equimolar amounts of one or more BNP fragments in which the amino terminus has lost from 1 to 9 residues, and wherein said assay in step (b), if performed, is configured such that pro-BNP is detected with at least a 5-fold reduction in signal relative to equimolar amounts of one or more pro-BNP fragments in which the amino terminus has lost from 1 to 10 residues.

2. A method according to claim 1, wherein said assay in step (b) is configured such that pro-BNP is detected with at least a 10-fold reduction in signal relative to equimolar amounts of one or more pro-BNP fragments in which the amino terminus has lost from 1 to 10 residues.

3. A method according to claim 1, wherein said assay in step (b) is configured such that pro-BNP is detected with at least a 5-fold reduction in signal relative to equimolar amounts of $BNP_{3-108}$.

4. A method according to claim 3, wherein said assay in step (b) is configured such that $BNP_{5-108}$ is detected with at least a 5-fold reduction in signal relative to equimolar amounts of $BNP_{3-108}$.

5. A method according to claim 1, wherein said assay in step (b) is configured to provide a signal that is insensitive to one or more pro-BNP related species selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$, but that exhibit at least a 5-fold reduction in signal from an equimolar amount of $BNP_{1-108}$.

6. A method according to claim 1, wherein said assay in step (b) is configured to provide a 5-fold greater signal from an amount of $BNP_{1-108}$, compared to an equimolar amount of one or more pro-BNP related species selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$.

7. A method according to claim 1, wherein said assay in step (a) is configured such that BNP is detected with at least a 10-fold reduction in signal relative to equimolar amounts of one or more BNP fragments in which the amino terminus has lost from 1 to 9 residues.

8. A method according to claim 1, wherein said assay in step (a) is configured to provide a signal that is insensitive to one or more BNP related species selected from the group consisting of $BNP_{79-108}$, $BNP_{81-108}$, $BNP_{83-108}$, $BNP_{79-106}$, $BNP_{81-106}$, and $BNP_{83-106}$, but that exhibit at least a 5-fold reduction in signal from an equimolar amount of $BNP_{77-108}$.

9. A method according to claim 1, wherein said assay in step (a) is configured to provide a 5-fold greater signal from an amount of $BNP_{77-108}$, compared to an equimolar amount of one or more BNP related species selected from the group consisting of $BNP_{79-108}$, $BNP_{81-108}$, $BNP_{83-108}$, $BNP_{79-106}$, $BNP_{81-106}$, and $BNP_{83-106}$.

10. A method according to claim 1, wherein the subject is a human.

11. A method according to claim 1, wherein said assaying step (a) comprises contacting said sample with an antibody selected to distinguish between BNP and one or more BNP related fragments selected from the group consisting of $BNP_{79-108}$, $BNP_{81-108}$, $BNP_{83-108}$, $BNP_{79-106}$, $BNP_{81-106}$, and $BNP_{83-106}$; or said assaying step (b) comprises contacting said sample with an antibody selected to distinguish between pro-BNP and one or more pro-BNP related fragments selected from the group consisting of $BNP_{3-108}$, $BNP_{5-108}$, $BNP_{7-108}$, $BNP_{3-76}$, $BNP_{5-76}$, $BNP_{7-76}$, $BNP_{1-106}$, $BNP_{3-106}$, $BNP_{5-106}$, and $BNP_{7-106}$.

12. A method according to claim 11, wherein said assaying step (a) or (b) comprises performing an immunoassay.

13. A method according to claim 11, wherein said assaying step (a) or (b) comprises performing mass spectrometry.

14. A method according to claim 1, wherein said assaying step (a) or (b) comprises performing mass spectrometry.

15. A method according to claim 1, further comprising removal of one or more covalently bound carbohydrate residues from one or more of said BNP related species or pro-BNP related species of interest prior to said assaying step.

16. A method according to claim 15, wherein said removal of one or more covalently bound carbohydrate residues from one or more of said BNP related species or pro-BNP related species of interest provides an increased detection of one or more of said BNP related species or pro-BNP related species of interest by mass spectrometry.

17. A method according to claim 15, wherein said removal of one or more covalently bound carbohydrate residues from one or more of said BNP related species or pro-BNP related species of interest removes at least 80% of carbohydrate residues from one or more of said BNP related species or pro-BNP related species of interest.

* * * * *

SEQUENCE LISTING

<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly

-continued

```
                 1               5                  10                  15
Leu Gln Glu Gln Arg Asn His Leu Gln Gly Lys Leu Ser Glu Leu Gln
                     20                  25                  30

Val Glu Gln Thr Ser Leu Glu Pro Leu Gln Glu Ser Pro Arg Pro Thr
         35                  40                  45

Gly Val Trp Lys Ser Arg Glu Val Ala Thr Glu Gly Ile Arg Gly His
     50                  55                  60

Arg Lys Met Val Leu Tyr Thr Leu Arg Ala Pro Arg Ser Pro Lys Met
 65                  70                  75                  80

Val Gln Gly Ser Gly Cys Phe Gly Arg Lys Met Asp Arg Ile Ser Ser
                 85                  90                  95

Ser Ser Gly Leu Gly Cys Lys Val Leu Arg Arg His
            100                 105
```

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
His Pro Leu Gly Ser Pro Gly Ser Cys
 1               5
```

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
His Pro Leu Gly Ser Pro Gly Ser Ala Ser Asp Leu Cys
 1               5                  10
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Leu Gly Ser Pro Gly Ser Ala Ser Cys
 1               5
```

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Leu Gly Ser Pro Gly Ser Ala Ser Asp Leu Glu Thr Cys
 1               5                  10
```